(12) United States Patent
Nagler et al.

(10) Patent No.: US 11,883,444 B2
(45) Date of Patent: Jan. 30, 2024

(54) INHIBITION OF ENTERIC INFECTION THROUGH THE MODULATION OF MICROBIOTA

(71) Applicants: The University of Chicago, Chicago, IL (US); The Regents of the University of Michigan, Ann Arbor, MI (US)

(72) Inventors: Cathyrn R. Nagler, Chicago, IL (US); Gabriel Nunez, Ann Arbor, MI (US); Yun-Gi Kim, Ann Arbor, MI (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 17/812,873

(22) Filed: Jul. 15, 2022

(65) Prior Publication Data
US 2023/0158085 A1    May 25, 2023

Related U.S. Application Data

(63) Continuation of application No. 16/476,216, filed as application No. PCT/US2018/012481 on Jan. 5, 2018, now Pat. No. 11,400,121.

(Continued)

(51) Int. Cl.
| | | |
|---|---|---|
| A61K 35/742 | (2015.01) | |
| A23K 50/75 | (2016.01) | |
| A23K 10/18 | (2016.01) | |
| A23L 33/135 | (2016.01) | |
| A23L 33/00 | (2016.01) | |

(Continued)

(52) U.S. Cl.
CPC ............ *A61K 35/742* (2013.01); *A23K 10/18* (2016.05); *A23K 50/75* (2016.05); *A23L 33/135* (2016.08); *A23L 33/40* (2016.08); *A61K 9/0031* (2013.01); *A61K 9/0053* (2013.01); *A61K 9/0056* (2013.01); *A61K 31/194* (2013.01); *A61K 45/06* (2013.01); *A61P 31/04* (2018.01); *C12Q 1/689* (2013.01); *A23V 2002/00* (2013.01); *A61K 2035/115* (2013.01); *C12Q 2600/158* (2013.01)

(58) Field of Classification Search
CPC .................................................... A61K 35/742
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |

(Continued)

FOREIGN PATENT DOCUMENTS

| | | |
|---|---|---|
| WO | WO 2001/093904 A1 | 12/2001 |
| WO | WO 2014/121301 A1 | 8/2014 |
| WO | WO 2016/086209 | 6/2016 |

OTHER PUBLICATIONS

Cartman, "Time to consider Clostridium probiotics?" Future Microbiol 6(9):969-971, 2011.*

(Continued)

*Primary Examiner* — Rosanne Kosson
(74) *Attorney, Agent, or Firm* — David W. Staple

(57) ABSTRACT

Provided herein are compositions and methods for the inhibition of enteric infection. In particular, compositions comprising bacteria of the class Clostridia are administered to human and/or animal subjects to prevent or decrease susceptibility to enteric infection.

18 Claims, 19 Drawing Sheets
Specification includes a Sequence Listing.

Related U.S. Application Data

(60) Provisional application No. 62/442,527, filed on Jan. 5, 2017.

(51) Int. Cl.
| | |
|---|---|
| *A61P 31/04* | (2006.01) |
| *A61K 9/00* | (2006.01) |
| *A61K 31/194* | (2006.01) |
| *A61K 45/06* | (2006.01) |
| *C12Q 1/689* | (2018.01) |
| *A61K 35/00* | (2006.01) |

(56) References Cited

U.S. PATENT DOCUMENTS

| | | | |
|---|---|---|---|
| 6,627,067 | B1 | 9/2003 | Branton et al. |
| 7,238,485 | B2 | 7/2007 | Akeson et al. |
| 7,258,838 | B2 | 8/2007 | Li et al. |
| 2004/0127403 | A1 | 7/2004 | Parenti et al. |
| 2006/0003171 | A1 | 1/2006 | Igawa et al. |
| 2009/0029477 | A1 | 1/2009 | Meller et al. |
| 2010/0291100 | A1 | 11/2010 | Macinga |
| 2019/0388483 | A1 | 12/2019 | Nagler et al. |

OTHER PUBLICATIONS

Appleby et al., New technologies for ultra-high throughput genotyping in plants. Methods Mol Biol. 2009;513:19-39.
Borenshtein et al., Utility of the Citrobacter rodentium infection model in laboratory mice. Curr Opin Gastroenterol. Jan. 2008;24(1):32-7.
Dieleman et al., Chronic experimental colitis induced by dextran sulphate sodium (DSS) is characterized by Th1 and Th2 cytokines. Clin Exp Immunol. Dec. 1998;114(3):385-91.
Figueira et al., Functions of the *Salmonella* pathogenicity island 2 (SPI-2) type III secretion system effectors. Microbiology (Reading). May 2012;158(Pt 5):1147-1161.
Fox et al., Applications of ultra-high-throughput sequencing. Methods Mol Biol. 2009;553:79-108.
Garrity et al. The Taxonomic Outline of Bacteria and Archaea. TOBA Release 7.7,Michigan State University Board of Trustees, Mar. 2007.
Guo et al., Taxonomic precision of different hypervariable regions of 16S rRNA gene and annotation methods for functional bacterial groups in biological wastewater treatment. PLoS One. Oct. 16, 2013;8(10):e76185.
Hamady M et al., Microbial community profiling for human microbiome projects: Tools, techniques, and challenges. Genome Res. 2009; 19:1141.
Hasegawa et al., Transitions in oral and intestinal microflora composition and innate immune receptor-dependent stimulation during mouse development. Infect Immun. Feb. 2010;78(2):639-50.
Hirayama et al., Metabolic profiling reveals new serum biomarkers for differentiating diabetic nephropathy. Anal Bioanal Chem. Dec. 2012;404(10):3101-9.
Imelfort et al., De novo sequencing of plant genomes using second-generation technologies. Brief Bioinform. Nov. 2009;10(6):609-18.
Kamada et al., Role of the gut microbiota in immunity and inflammatory disease. Nat Rev Immunol. May 2013;13(5):321-35.
Kollman et al., Innate immune function by Toll-like receptors: distinct responses in newborns and the elderly. Immunity. Nov. 16, 2012;37(5):771-83.
Komboj et al., bClostridium difficile infection after allogeneic hematopoietic stem cell transplant: strain diversity and outcomes associated with NAP1/027. Biol Blood Marrow Transplant. Oct. 2014;20(10):1626-33.
Kozich et al., Development of a dual-index sequencing strategy and curation pipeline for analyzing amplicon sequence data on the MISeq Illumina sequencing platform. Appl. Environ Microbiol. Sep. 2013;79(17):5112-20.
Lanata et al., Global causes of diarrheal disease mortality in children <5 years of age: a systematic review. PLoS One. Sep. 4, 2013;8(9):e72788.
Margulies et al., Genome sequencing in microfabricated high-density picolitre reactors. Nature. Sep. 15, 2005;437(7057):376-80.
Matsuda et al., Establishment of an analytical system for the human fecal microbiota, based on reverse transcription-quantitative PCR targeting of multicopy rRNA molecules. Appl Environ Microbiol Apr. 2009;75(7):1961-9.
McKenney et al., From Hype to Hope: The Gut Microbiota in Enteric Infectious Disease. Cell. Dec. 3, 2015;163(6):1326-32.
Morozawa et al., Applications of next-generation sequencing technologies in functional genomics. Genomics. Nov. 2008;92(5):255-64.
Ochman et al., Identification of a pathogenicity island required for *Salmonella* survival in host cells. Proc Natl Acad Sci U S A. Jul. 23, 1996;93(15):7800-4.
Palmer et al., Development of the human infant intestinal microbiota PLoS Biol Jul. 2007;5(7):e177.
Pearson, Rapid and sensitive sequence comparison with FASTP and FASTA. Methods Enzymol. 1990;183:63-98.
Peterson et al., Detection of toxigenic Clostridium difficile in stool samples by real-time polymerase chain reaction for the diagnosis of C. -difficile-associated diarrhea. Clin Infect Dis. Nov. 1, 2007;45(9):1152-60.
Prabhudas et al., Challenges in infant immunity: implications for responses to infection and vaccines. Nat Immunol. Mar. 2011;12(3):189-94.
Ronaghi et al., Real-time DNA sequencing using detection of pyrophosphate release. Anal Biochem. Nov. 1, 1996;242(1):84-9.
Schloss et al., Introducing mothur: open-source, platform-independent, community-supported software for describing and comparing microbial communities. Appl Environ Microbiol. Dec. 2009;75(23):7537-41.
Shendure et al., Accurate multiplex polony sequencing of an evolved bacterial genome. Science. Sep. 9, 2005;309(5741):1728-32.
Soergel et al., Selection of primers for optimal taxonomic classification of environmental 16S rRNA gene sequences. ISME J. Jul. 2012;6(7):1440-4.
Soni et al., Progress toward ultrafast DNA sequencing using solid-state nanpores. Clin Chem Nov. 2007;53(11):1996-2001.
Stefka et al., Commensal bacteria protect against food allergen sensitization. Proc Natl Acad Sci U S A. Sep. 9, 2014;111(36):13145-50.
Sugimoto et al., Capillary electrophoresis mass spectrometry-based saliva metabolomics indentified oral, breast and pancreatic cancer-specific profiles. Metabolomics. Mar. 2010;6(1):78-95.
Tanoue et al., Development and maintenance of intestinal regulatory T cells. Nat Rev Immunol May 2016;16(5):295-309.
Wang et al., Naive Bayesian classifier for rapid assignment of rRNA sequences into the new bacterial taxonomy. Appl Environ Microbiol Aug. 2007;73(16):5261-7
Woese et al., Towards a natural system of organisms: proposal for the domains Archaea, Bacteria, and Eucarya. Proc Natl Acad Sci U S A. Jun. 1990;87(12):4576-9.
International Search Report and Written Opinion for PCT/US2018/012481, dated Mar. 12, 2018. 11 pages.

\* cited by examiner

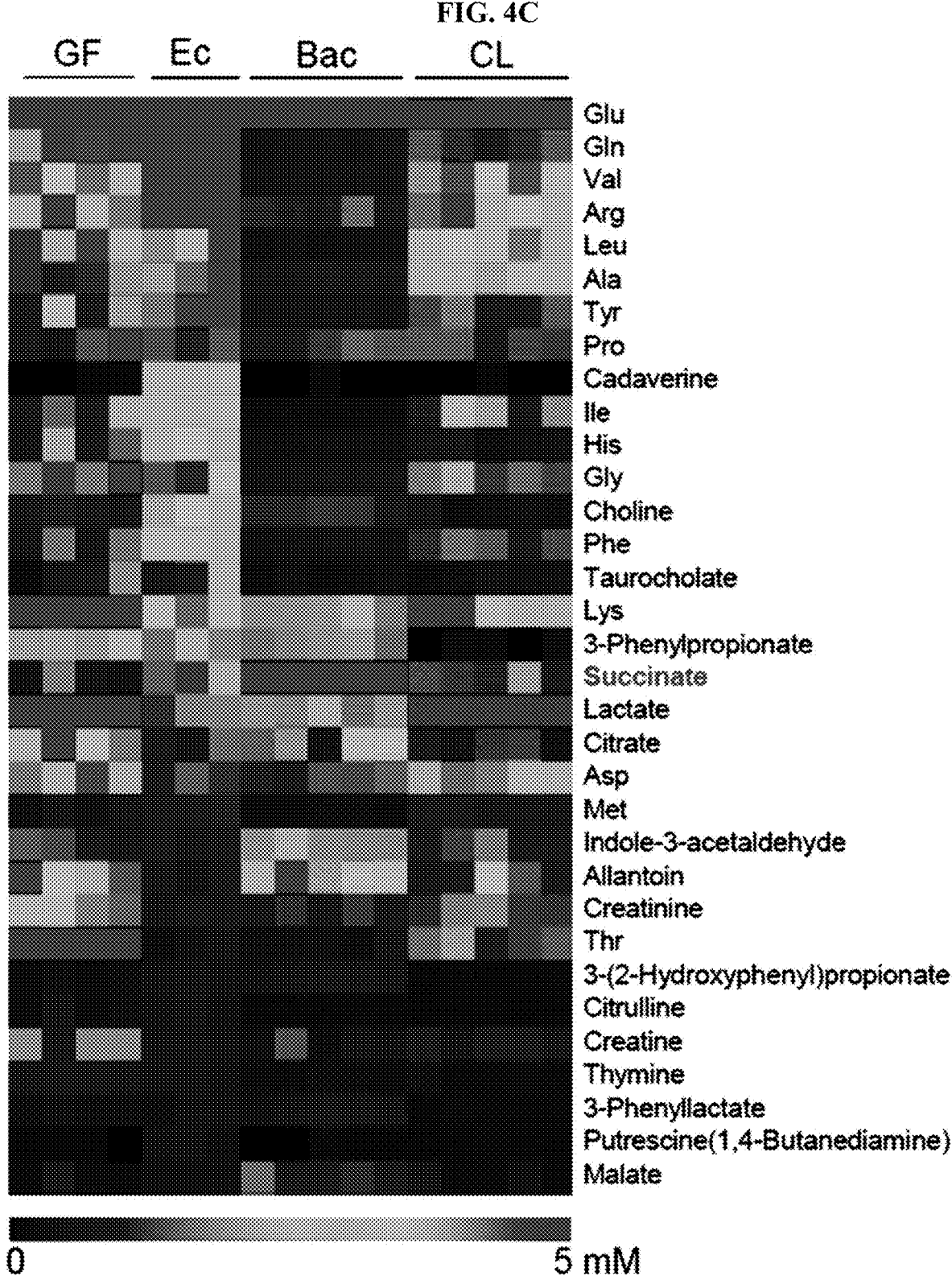

FIG. 5A
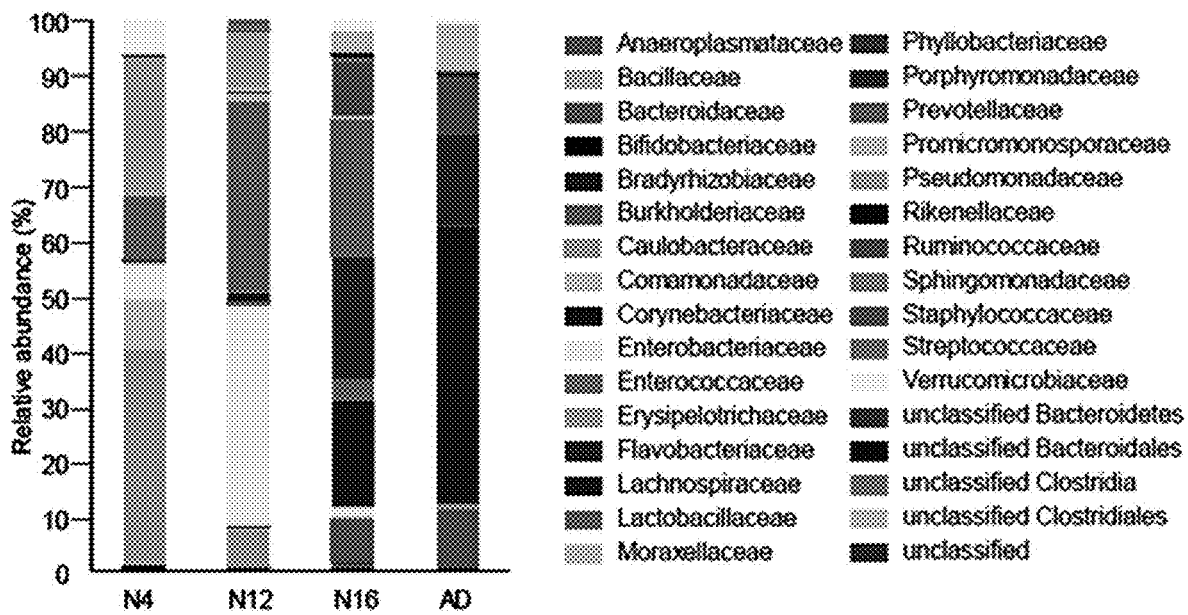
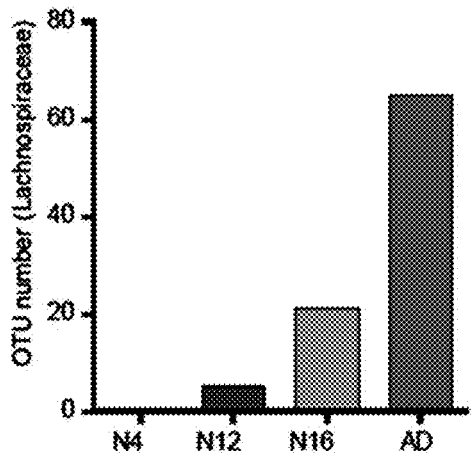
FIG. 5B
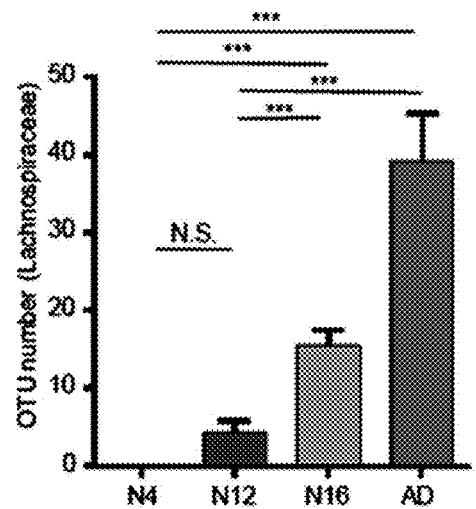
FIG. 5C

INHIBITION OF ENTERIC INFECTION THROUGH THE MODULATION OF MICROBIOTA

CROSS-REFERENCE TO RELATED APPLICATIONS

The present invention is a continuation of U.S. patent application Ser. No. 16/476,216, filed Jul. 5, 2019, now allowed, which is a § 371 National Entry of PCT/US2018/012481, filed Jan. 5, 2018, which claims priority to U.S. Provisional Patent Application Ser. No. 62/442,527, filed Jan. 5, 2017, each of which is incorporated by reference in its entirety.

STATEMENT REGARDING FEDERAL FUNDING

This invention was made with government support under grant numbers DK091191, DK061707, AI106302 and DK095782 awarded by the National Institutes of Health. The government has certain rights in the invention.

SEQUENCE LISTING

The text of the computer readable sequence listing filed herewith, titled "34936-304_SEQUENCE_LISTING", created Feb. 10, 2023, having a file size of 4,583 bytes, is hereby incorporated by reference in its entirety.

FIELD

Provided herein are compositions and methods for the inhibition of enteric infection. In particular, compositions comprising bacteria of the class Clostridia are administered to human and/or animal subjects to prevent or decrease susceptibility to enteric infection.

BACKGROUND

Newborns and children less than 1 year old are highly susceptible to frequent infection by bacterial pathogens via the oral route (refs. 1, 2; each incorporated by reference in its entirety). The increased susceptibility to infections has been generally ascribed to immaturity of the innate and adaptive immune systems; however, additional factors may play an important role because immune responses to different stimuli are highly variable among neonates (ref. 3; incorporated by reference in its entirety).

SUMMARY

The technology provided herein relates to compositions (e.g., pharmaceutical compositions), methods, kits, and systems for the inhibition of enteric infection (e.g., in a subject, e.g., a human, an animal (e.g., a livestock animal), etc.). In particular, compositions comprising bacteria of the class Clostridia (e.g., bacteria of the order Clostridiales, bacteria of the genus *Clostridium*, etc.) are administered to human and/or animal subjects to prevent or decrease susceptibility to enteric infection. Bacteria may be administered in any suitable state, for example, live (e.g., vegetative), freeze-dried, spores, etc. Accordingly, provided herein are technologies related to a method of preventing enteric infection in a subject. In some embodiments, the technology provides a method comprising administering a composition comprising bacteria of the class Clostridia to the subject. In some embodiments, methods comprise administering a composition comprising at least $10^4$ colony forming units (CFU) (e.g., at least $1 \times 10^4$ CFU, $2 \times 10^4$ CFU, $5 \times 10^4$ CFU, $1 \times 10^5$ CFU, $2 \times 10^5$ CFU, $5 \times 10^5$ CFU, $1 \times 10^6$ CFU, $2 \times 10^6$ CFU, $5 \times 10^6$ CFU, $1 \times 10^7$ CFU, $2 \times 10^7$ CFU, $5 \times 10^7$ CFU, $1 \times 10^8$ CFU, $2 \times 10^8$ CFU, $5 \times 10^8$ CFU, $1 \times 10^9$ CFU, $2 \times 10^9$ CFU, $5 \times 10^9$ CFU, $1 \times 10^{10}$ CFU, $2 \times 10^{10}$ CFU, $5 \times 10^{10}$ CFU, $1 \times 10^{11}$ CFU, $2 \times 10^{11}$ CFU, $5 \times 10^{11}$ CFU, $1 \times 1012$ CFU, $2 \times 10^{12}$ CFU, $5 \times 10^{12}$ CFU, or more or ranges therebetween) of Clostridia. In some embodiments, methods comprise administering a composition comprising bacteria spores. In some embodiments, methods comprise administering a composition comprising at least $10^2$ Clostridia spores (e.g., at least $1 \times 10^2$ CFU, $2 \times 10^2$ CFU, $5 \times 10^2$ CFU, $1 \times 10^3$ CFU, $2 \times 10^3$ CFU, $5 \times 10^3$ CFU, $1 \times 10^4$ CFU, $2 \times 10^4$ CFU, $5 \times 10^4$ CFU, $1 \times 10^5$ CFU, $2 \times 10^5$ CFU, $5 \times 10^5$ CFU, $1 \times 10^6$ CFU, $2 \times 10^6$ CFU, $5 \times 10^6$ CFU, $1 \times 10^7$ CFU, $2 \times 10^7$ CFU, $5 \times 10^7$ CFU, $1 \times 10^8$ CFU, $2 \times 10^8$ CFU, $5 \times 10^8$ CFU, $1 \times 10^9$ CFU, $2 \times 10^9$ CFU, $5 \times 10^9$ CFU, $1 \times 10^{10}$ CFU, $2 \times 10^{10}$ CFU, $5 \times 10^{10}$ CFU, $1 \times 10^{11}$ CFU, $2 \times 10^{11}$ CFU, $5 \times 10^{11}$ CFU, $1 \times 10^{12}$ CFU, $2 \times 10^{12}$ CFU, $5 \times 10^{12}$ CFU, or more or ranges therebetween).

Methods are provided for the treatment of subjects in need of treatment with bacteria of the class Clostridia. For example, in some embodiments methods comprise treating a subject having or at risk for having an enteric infection. In some exemplary embodiments, methods comprise treating a subject who has an abnormal gut microbiota or a pathogenic gut microbiota, e.g., methods comprise administering a composition comprising bacteria of the class Clostridia to a subject who has an abnormal gut microbiota or a pathogenic gut microbiota. In some exemplary embodiments, methods comprise treating a subject who has a gut microbiota that differs from the normal microbiota in one or both of membership or relative abundance of one or more members of the gut microbiota, e.g., methods comprise administering a composition comprising bacteria of the class Clostridia to a subject who has a gut microbiota that differs from the normal microbiota in one or both of membership or relative abundance of one or more members of the gut microbiota. In some embodiments, the technology relates to methods comprising treating a subject that has a gut microbiota that differs from the normal microbiota in the membership or relative abundance of Clostridia, e.g., methods comprising administering a composition comprising bacteria of the class Clostridia to a subject who has a gut microbiota that differs from the normal microbiota in the membership or relative abundance of Clostridia.

The technology is not limited in the types or classes of subjects or patients that are treated and/or that are administered the compositions comprising bacteria of the class Clostridia. For example, in some embodiments the subject is a human. In some embodiments, the subject is a young human, e.g., that has not developed a gut microbiota that protects the young human from enteric infection. For example, in some embodiments the subject is a human infant or a human neonate or a human newborn. The technology is applicable to subjects and patients that are nonhuman, e.g., mammals, birds, etc., including but not limited to livestock animals, domesticated animals, animals in captivity, etc. In some embodiments, the subject is a chicken, cow, goat, pig, or sheep. In some embodiments, the subject is a nonhuman infant, neonate, newborn, e.g., according to veterinary practices by which said terms are associated with a particular animal's age. In some embodiments, the subject is a non-human animal that has an age of 1 to 60 minutes (e.g., 1, 2, 3, 5, 10, 15, 20, 25, 30, 35, 40, 45, 50, 55, 60 minutes old, e.g., 1, 2, 3, 5, 10, 15, 20, 25, 30, 35, 40, 45, 50, 55, 60 minutes after birth); in some embodiments, the subject is a nonhuman animal that has an age of from 1 to 24 hours (e.g., 1, 2, 3, 4, 5, 6, 7, 8, 9, 10, 12, 13, 14, 15, 16, 17, 18, 19, 20, 21, 22, 23, 24 hours, e.g., 1, 2, 3, 4, 5, 6, 7, 8, 9, 10, 12, 13, 14, 15, 16, 17, 18, 19, 20, 21, 22, 23, 24 hours after birth); in some embodiments the subject is a nonhuman animal that has an age of 1 day, 2, days, 3, days, 4 days, 5 days, 6 days, 1 week, 2 weeks, 3 weeks, one month, or 2 months of age, although other ages are specifically contemplated. In some embodiments, the subject is a human that has an age of 1 to 60 minutes (e.g., 1, 2, 3, 5, 10, 15, 20, 25, 30, 35, 40, 45, 50, 55, 60 minutes old, e.g., 1, 2, 3, 5, 10, 15, 20, 25, 30, 35, 40, 45, 50, 55, 60 minutes after birth); in some embodiments, the subject is a human that has an age of from 1 to 24 hours (e.g., 1, 2, 3, 4, 5, 6, 7, 8, 9, 10, 12, 13, 14, 15, 16, 17, 18, 19, 20, 21, 22, 23, 24 hours, e.g., 1, 2, 3, 4, 5, 6, 7, 8, 9, 10, 12, 13, 14, 15, 16, 17, 18, 19, 20, 21, 22, 23, 24 hours after birth); in some embodiments the subject is a human that has an age of 1 day, 2, days, 3, days, 4 days, 5 days, 6 days, 1 week, 2 weeks, 3 weeks, one month, or 2 months of age, although other ages are specifically contemplated.

In some embodiments, the subject is a juvenile, adult, or elderly subject.

In some embodiments, the subject has an abnormal or pathogenic gut microbiota due to having previously been treated with antibiotics. In some embodiments, the subject has an abnormal or pathogenic gut microbiota due to current treatment with antibiotics. In some embodiments, the subject is considered to be at risk of having an abnormal or pathogenic gut microbiota due to future treatment with antibiotics. In some embodiments, the subject has undergone a stem cell transplant or will have a stem cell transplant in the future.

The technology is not limited in the type or route if administration. In some embodiments, the type or route of administration provides the composition comprising bacteria of the class Clostridia to the subject's gastrointestinal tract. For example, in some embodiments the composition is administered orally and in some embodiments the composition is administered rectally.

Some embodiments comprise administering compositions comprising bacteria of the class Clostridia and one or more additional components. In some embodiments, the composition further comprises succinate. Some embodiments comprise administering compositions comprising bacteria of the class Clostridia and administering another composition comprising succinate to the subject (e.g., before, after, or concurrently with compositions comprising bacteria of the class Clostridia).

In some embodiments, the technology comprises testing a subject or a patient. For example, some embodiments comprise testing the subject for the presence, absence, or amount of Clostridia in the gut microbiota. Some embodiments comprise testing the subject for an enteric infection. Some embodiments comprise testing the subject for an abnormal gut microbiota. Some embodiments comprise testing the subject for a pathogenic gut microbiota. The technology provides methods in which a subject or a patient is tested before and/or after administration of a composition comprising bacteria of the class Clostridia to the subject or patient. In some embodiments, the testing informs the dose amount, dose schedule, and/or CFU of Clostridia in the composition that is administered to the subject or patient. Some embodiments comprise administration of a composition comprising bacteria of the class Clostridia to the subject or patient, testing the subject or patient, and a second administration of a composition comprising bacteria of the class Clostridia to the subject. The first and second administrations and/or compositions may be the same or different, e.g., same or different in dose, amount, route, composition, species of Clostridia, CFU of Clostridia, etc. Some embodiments herein include testing the subject or patient for enteric infection; abnormal gut microbiota; pathogenic microbiota; or presence, absence, number, or relative abundance of Clostridia in the gut microbiota. In some embodiments, such testing comprises: analysis of a biomarker such as a metabolite, nucleic acid, polypeptide, sugar, lipid, indication, symptom, etc. For example, in some embodiments the technology comprises testing using a labeled probe, a nucleic acid test (NAT), a nucleic acid amplification test (NAAT), a nucleic acid amplification technology (e.g., polymerase chain reaction (e.g., PCR, real-time PCR, probe hydrolysis PCR, reverse transcription PCR), isothermal amplification (e.g., nucleic acid sequence-based amplification (NASBA)), a ligase chain reaction, or a transcription mediated amplification, etc.), or nucleic acid sequencing (e.g., Sanger sequencing or next-gen (e.g., second generation, third generation, etc.) sequencing methods including, e.g., sequencing-by-synthesis, single molecule sequencing, nanopore, ion torrent, etc.).

Some embodiments comprise a second testing of the subject or patient, which may be the same or different from the first testing of the patient. The second testing may comprise testing the subject or patient for the presence, absence, or amount of Clostridia in the gut microbiota; testing the subject for an enteric infection; testing the subject for an abnormal gut microbiota; and/or testing the subject for a pathogenic gut microbiota. In some embodiments, the second testing occurs after administration of a composition comprising bacteria of the class Clostridia to the subject. In some embodiments, the second testing indicates that the administration of the composition comprising bacteria of the class Clostridia to the subject is an effective treatment. In some embodiments, the second testing indicates that the administration of the composition comprising bacteria of the class Clostridia to the subject was an ineffective treatment. In some embodiments, the dose amount, dose schedule, and/or type or CFU of Clostridia in the composition is changed for subsequent administrations to the subject or patient based on the results of the test.

In some embodiments, methods comprise administering to a subject or patient a composition comprising bacteria of the class Clostridia and a probiotic component or a prebiotic component.

The technology also comprises, in some embodiments, pharmaceutical compositions comprising bacteria of the class Clostridia (e.g., spores, vegetative cells, etc.) and a pharmaceutically acceptable carrier. In some embodiments, the pharmaceutical composition comprises an effective amount of Clostridia. Also, in some embodiments, the pharmaceutical composition comprises additional components, e.g., in some embodiments the pharmaceutical composition comprises a probiotic or a prebiotic. In some embodiments, the pharmaceutical composition further comprises succinate.

Non-limiting examples of prebiotics useful in the compositions and methods herein include xylose, arabinose, ribose, galactose, rhamnose, cellobiose, fructose, lactose, salicin, sucrose, glucose, esculin, tween 80, trehalose, maltose, mannose, melibiose, raffinose, fructooligosaccharides (e.g., oligofructose, inulin, inulin-type fructans), galactooligosaccharides, amino acids, alcohols, water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose), water-insoluble cellulose derivatives (most preferably, ethyl cellulose), unprocessed oatmeal, metamucil, all-bran, and any combinations thereof.

Embodiments provide that pharmaceutical compositions are formulated for administration to a subject or a patient, e.g., some embodiments provide pharmaceutical compositions formulated for administration to a human. Some embodiments provide pharmaceutical compositions formulated for administration to a human newborn, neonate, or infant. Some embodiments provide pharmaceutical compositions for administration to a livestock animal, e.g., a chicken, cow, goat, pig, or sheep.

Related embodiments provide a pharmaceutical composition comprising live bacteria and/or bacterial spores from the class Clostridia.

Embodiments provide pharmaceutical compositions formulated for various routes of administration, e.g., for providing the bacteria from the class Clostridia to the gastrointestinal tract. For example, in some embodiments, the pharmaceutical composition is formulated for oral administration and in some embodiments the pharmaceutical composition is formulated for rectal administration. In some embodiments, the pharmaceutical composition is a nutraceutical or a food.

Related embodiments provide kits comprising a pharmaceutical composition comprising bacteria from the class Clostridia or as otherwise described herein. Some embodiments provide a kit for treating enteric infection in a subject, the kit comprising a composition comprising bacteria of the class Clostridia formulated for administration to the subject; and a reagent for testing the membership or relative abundance of one or more members of the gut microbiota of the subject. In some embodiments, the kit reagent comprises a labeled oligonucleotide probe. In some embodiments, the kit reagent comprises an amplification oligonucleotide. Embodiments of kits comprise a reagent that provides a test for the presence, absence, or level of Clostridia in the gut microbiota of the subject; a test for the membership or relative abundance of Clostridia in the gut microbiota of the subject; and/or a test for the presence, absence, or level of a pathogen causative of enteric disease.

Some embodiments provide use of a composition comprising bacteria of the class Clostridia to treat a subject. Some embodiments provide use of a composition comprising bacteria of the class Clostridia to manufacture a medicament for administration to a subject. Some embodiments provide use of a composition comprising bacteria of the class Clostridia to treat or prevent enteric infection in a subject.

Some embodiments provide a system for treating enteric infection in a subject, the system comprising a composition comprising bacteria of the class Clostridia formulated for administration to the subject; and a reagent for testing the membership or relative abundance of one or more members of the gut microbiota of the subject. In some embodiments, the reagent comprises a labeled oligonucleotide probe. In some embodiments, the reagent comprises an amplification oligonucleotide. Embodiments of systems comprise a reagent that provides a test for the presence, absence, or level of Clostridia in the gut microbiota of the subject; a test for the membership or relative abundance of Clostridia in the gut microbiota of the subject; and/or a test for the presence, absence, or level of a pathogen causative of enteric disease.

Some embodiments provide a kit for treating enteric infection in a subject, the kit comprising a composition comprising bacteria of the class Clostridia formulated for administration to the subject; and a reagent for testing the membership or relative abundance of one or more members of the gut microbiota of the subject. In some embodiments, the kit reagent comprises a labeled oligonucleotide probe. In some embodiments, the kit reagent comprises an amplification oligonucleotide. Embodiments of kits comprise a reagent that provides a test for the presence, absence, or level of Clostridia in the gut microbiota of the subject; a test for the membership or relative abundance of Clostridia in the gut microbiota of the subject; and/or a test for the presence, absence, or level of a pathogen causative of enteric disease.

BRIEF DESCRIPTION OF THE FIGURES

FIG. 1A, Relative abundance of operational taxonomic units (OTUs) in fecal samples from GF mice reconstituted with cecal contents of 4-day old (N4) (n=8), 12-day old (N12) (n=4), 16-day old (N16) (n=4) or 7-week old (AD) (n=7) mice. Analysis was performed on day 21 post-reconstitution. Colors correspond to families. Data are from three independent experiments. FIG. 1B, Shannon's diversity index of fecal samples from GF reconstituted mice. Results are means±SD. Pooled data from three independent experiments shown in FIG. 1A. ***; $p<0.001$, Dunnett's multiple comparisons test. FIGS. 1C-1E, Age and gender-matched adult GF mice reconstituted with N4 microbiota (M-Neonate) or AD microbiota (M-Adult) were infected with *S. Typhimurium* ΔspiA. FIG. 1C, Mouse survival over time after infection of M-Neonate (n=16) and M-Adult (n=11) mice. Data are from two independent experiments. Log-rank test. FIG. 1D, Representative histology of hematoxylin and eosin (HE)-stained cecal sections from infected M-Neonate and M-Adult mice. Cecal tissue was processed 1 day after infection. High power images of marked area are shown in inset. Scale bar, 100 µm. FIG. 1E, Histopathological scores of cecal tissue from M-Neonate and M-Adult mice infected with *S. Typhimurium*. Each dot represents an individual mouse (M-Neonate; n=8, M-Adult; n=5). Data are from two independent experiments. ***; $P<0.001$, Mann-Whitney U test. FIG. 1F, Adult GF mice reconstituted with indicated microbiota were infected with *S. Typhimurium* ΔspiA. Pathogen loads (CFU/gram) in feces were determined one day after infection by plating. Each dot represents an individual mouse. Data are pooled from two independent experiments (n=8 per each group). ***; $P<0.001$ vs GF mice, Dunnett's multiple comparisons test. FIG. 1G, GF mice reconstituted with N4, N12, N16 and AD microbiota were infected with *C. rodentium*. CFU/gram of feces were determined on day 1, 3, 6, 12, 18, 24 and 30 after infection. Results are means±SD and are representative of three independent experiments (4-day old (N4) (n=4), 12-day old (N12) (n=5), 16-day old (N16) (n=4) or 7-week old (AD) (n=4) mice). ***; $P<0.001$ vs N4, Dunnett's multiple comparisons test.

FIG. 2A, GF mice reconstituted with cecal content of 4-day old mice (N4) were infected with *C. rodentium*. On day 30 after infection, the mice were cohoused with conventionally-raised mice (ratio of 1:1). Pathogen loads (CFU/gram of feces) were determined on the indicated days after cohousing. Each dot represents an individual mouse (n=7). Data were pooled from two independent experiments. ***; P<0.001 vs day 0, Dunnett's multiple comparisons test. FIG. 2B, Untreated or vancomycin-treated (Van) mice were infected with *C. rodentium*. Pathogen loads (CFU/gram) in feces were determined on day 1, 6, 12, 18, 24 and 30 after infection. Results are means±SD and representative of two experiments (n=5 per each group). ***; P<0.001 vs Untreated, Sidak's multiple comparisons test. FIG. 2C, Untreated or vancomycin-treated (Van) mice were infected with *S. Typhimurium* ΔspiA. Pathogen loads in fecal and cecal contents were determined on day 1 after infection. Each dot represents an individual mouse (n=8 per each group). Data are pooled from two independent experiments. ***; P<0.001, Mann-Whitney U test. FIG. 2D, Relative abundance of OTUs in fecal samples from adult mice fed a normal chow or lactose-cellobiose-rich (LC) diet for 21 days. Colors correspond to families. FIG. 2E, Adult mice fed a normal or LC diet for 21 days and then were infected with *S. Typhimurium* ΔspiA. Pathogen loads (CFU/gram) in fecal and cecal contents were determined on day 1 after infection. Each dot represents an individual mouse (n=7 per each group). Data are pooled from two independent experiments. ***; P<0.001, Mann-Whitney U test.

FIGS. 3A-3D, Adult GF mice reconstituted with microbiota of 4-day old mice (N4), N4 plus four *Bacteroides* species (Bac: *B. acidifaciens, B. thetaiotaomicron, B. vulgatus*, and *B. uniformis*) (N4+Bac), or N4 plus Clostridia consortium (N4+CL) were infected with *S. Typhimurium* ΔspiA and analyzed 1 day after infection. FIG. 3A, Pathogen loads (CFU/gram) in fecal and cecal contents were determined by plating. Each dot represents an individual mouse (N4; n=9, N4+Bac; n=8, N4+CL; n=13). Data are pooled from three independent experiments. *; P<0.001 vs N4, Dunnett's multiple comparisons test. FIG. 3B, Representative images of the large intestine of indicated mice 1 day after infection. Scale bar, 100 μm. FIG. 3C, Representative images of HE-stained cecal sections from N4, N4+Bac, and N4-CL mice. Cecal tissue was processed 1 day after infection. FIG. 3D, Histopathological scores of cecal tissue from indicated GF reconstituted mice. Each dot represents an individual mouse (N4; n=5, N4+Bac; n=7, N4+CL; n=10). Data are pooled from three independent experiments. *; P<0.001, N.S.; not significant, Dunnett's multiple comparisons test. FIG. 3E, Adult GF mice or GF mice reconstituted with 4-day old microbiota (N4) or N4 plus Clostridia consortium (N4+CL) were infected with *C. rodentium*. CFU/gram of feces were determined on day 1, 6, 12, 18, 24 and 30 after infection. Results are means±SD and representative of two experiments (n=4 per each group). ***; P<0.001 vs GF mice, Dunnett's multiple comparisons test. FIG. 3F, GF mice reconstituted with N4 microbiota were infected with *C. rodentium* (Cr). On day 30 post-infection, the mice were cohoused with GF mice (Control), or GF mice reconstituted with four *Bacteroides* species (Bac) or Clostridia consortium (CL). CFU/gram of feces were determined in feces on the indicated days after cohousing. Each dot represents an individual mouse (Control; n=7, Bac; n=8, CL; n=13). Data are pooled from three independent experiments. *; P<0.05, ***; P<0.001 vs Control, Dunnett's multiple comparisons test. FIG. 3G, 10-day old littermate mice were left untreated (Neonate) or given Clostridia consortium (Neonate+CL) by gavage and then infected with *S. Typhimurium* ΔspiA. Mouse survival was monitored over time after infection (Neonate (n=19) and Neonate+CL (n=19). P=0.0054 by Log-rank test.

FIGS. 4A-F. The neonatal microbiota increases the abundance of protective Clostridia in the gut. FIG. 4A, Analysis of the fecal microbiota from GF mice gavaged with Clostridia consortium (Control) or GF mice previously reconstituted with the cecal microbiota of 4-day old mice (N4) and then gavaged with Clostridia consortium. The presence of *Clostridium* cluster XIVa in fecal DNA was quantified over time by qPCR. Results were normalized to the amounts of *Clostridium* cluster XIVa DNA in fecal samples from mice bearing the Clostridia consortium. Each dot represents an individual mouse (Control; n=6, N4; n=9). Data pooled from three independent experiments. P<0.001 vs Control, Sidak's multiple comparisons test. FIG. 4B, Analysis of the fecal microbiota from GF mice gavaged with the Clostridia consortium (Control) or GF mice previously reconstituted with mouse *E. coli* (Ec) or *B. acidifaciens* (Bac). The presence of *Clostridium* cluster XIVa in fecal DNA was quantified by qPCR. Results were normalized to the amounts of *Clostridium* cluster XIVa DNA in fecal samples of Clostridia consortium. Each dot represents an individual mouse (Control; n=5, Ec; n=6, Bac; n=6). Data pooled from two independent experiments. P<0.001 vs Control, Sidak's multiple comparisons test. FIG. 4C, Heatmap analysis of top 33 metabolites in fecal samples from GF or GF mice reconstituted with *E. coli* (EC), *B. acidifaciens* (Bac), or Clostridia consortium (CL). FIG. 4D, Fecal microbiota from GF mice reconstituted with Clostridia consortium was gavaged into untreated GF mice (Control) or mice treated with 100 mM succinate (Suc), 50 mM lactate (Lac), or 100 mM acetate (Ace) for 7 days. Gavage of Clostridia consortium was performed on day 7 after treatment and metabolite administration was continued for another 14 days. The presence of *Clostridium* cluster XIVa in fecal DNA was monitored over time by qPCR. Each dot represents an individual mouse (n=6 per each group). Data pooled from two independent experiments. P<0.001 vs Control, Sidak's multiple comparisons test. FIG. 4E-F, Untreated GF mice (Control) or GF mice treated with succinate (Suc) for 7 days were given Clostridia consortium by gavage. The mice were then infected with *S. Typhimurium* ΔspiA and pathogen loads in fecal (E) and cecal (F) contents were determined one day after infection by plating. Each dot represents an individual mouse (Untreated; n=9, Suc; n=10). Data are pooled from three independent experiments. ***; P<0.001, Mann-Whitney U test.

FIGS. 5A-C. Composition of the microbiota in neonatal and adult cecal contents. FIG. 5A, Relative abundance of operational taxonomic units (OTUs) in the cecal content of day-4 old (N4), day-12 old (N12), day-16 old (N16) or 7-week old (AD) mice. Colors correspond to families. FIG. 5B, Number of Lachnospiraceae OTUs with relative abundance greater than 0.1% in the cecal content of N4, N12, N16 and AD mice used to reconstitute mice depicted in FIG. 1A and FIG. 5C. FIG. 5C. Number of Lachnospiraceae OTUs with relative abundance greater than 0.1% in fecal samples from GF mice reconstituted with cecal contents of N4, N12, N16 or AD mice. Results are means±SD. Data are pooled from the three independent experiments shown in FIG. 1A. ***; P<0.001, N.S.; not significant, Dunnett's multiple comparisons test.

FIG. 9A, Analysis of the fecal microbiota from GF mice gavaged with Clostridia consortium (Control) or GF mice previously reconstituted with the cecal microbiota of 4-day old (N4) mice and then gavaged with Clostridia consortium. The presence of *Clostridium* cluster IV in fecal DNA was quantitated over time by qPCR. Results were normalized to the amounts of *Clostridium* cluster XIVa DNA in fecal samples of Clostridia consortium. FIG. 9B, Analysis of the fecal microbiota from GF mice gavaged with Clostridia consortium (Control) or GF mice previously reconstituted with mouse *E. coli* (Ec) or *B. acidifaciens* (Bac). The presence of *Clostridium* cluster IV in fecal DNA was quantified by qPCR. Results were normalized to the amounts of *Clostridium* cluster XIVa DNA in fecal samples of Clostridia consortium. FIG. 9C, Fecal microbiota from GF mice reconstituted with Clostridia consortium was gavaged into untreated GF mice (Control) or mice treated with succinate (Suc), lactate (Lac), or acetate (Ace) for 7 days. Gavage of Clostridia consortium was performed on day 7 after treatment and metabolite administration was continued for another 14 days. The presence of *Clostridium* cluster IV in fecal DNA was monitored over time by quantitated by qPCR. Each dot represents an individual mouse. Data are pooled from three independent experiments. P<0.001 vs Control, Sidak's multiple comparisons test.

FIG. 10. The microbiota from 4-day old mice contribute to colonization of Clostridia species which protect mice from *Salmonella* infection. GF mice were reconstituted with the fecal microbiota of gnotobiotic mice harboring the Clostridia consortium alone (CL) or the cecal microbiota of day-4 old mice and 7 days later the mice were gavaged with the Clostridia consortium (N4+CL). Seven days after reconstitution, CL or NE4+CL mice were infected with *Salmonella* ΔspiA and mouse survival was monitored over time. P=0.0016 by Log-rank test.

DEFINITIONS

Figure 1A:
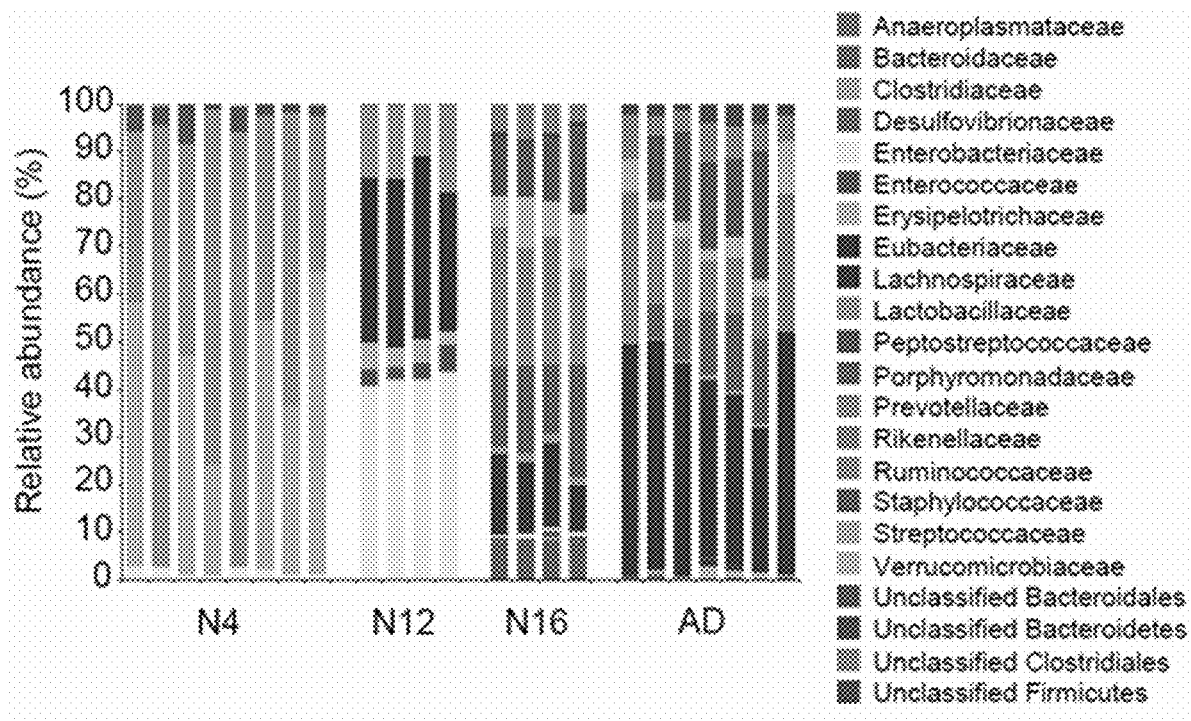
FIGS. 1A-G. The early neonatal microbiota lacks colonization resistance against enteric pathogens.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a Clostridia species" is a reference to one or more Clostridia species, unless the context clearly dictates otherwise.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry (e.g., chickens), fish, crustaceans, etc.). As used herein, the term "patient" typically refers to a subject that is being treated for a disease or condition.

As used herein, the term "infant", when referring to a human, refers to a human between the ages of 1 month and 12 months.

As used herein, the term "newborn", when referring to a human, is a human who is hours, days, or 1 to 3 weeks old.

As used herein, the term "neonate", when referring to a human, refers to a newborn human and humans having an age up to and including 28 days after birth. The term "neonate" also refers to premature infants, postmature infants, and full term infants.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., a pharmaceutical composition comprising Clostridia, and/or additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the term "microbe" refers to cellular prokaryotic and eukaryotic species from the domains Archaea, Bacteria, and Eukarya, the latter including yeast and filamentous fungi, protozoa, algae, or higher Protista, and encompasses both individual organisms and populations comprising any number of the organisms. The terms "microbial cells" and "microbes" are used interchangeably with the term "microorganism".

The term "prokaryotes" refers to cells that contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The terms "bacteria" and "bacterium" and "archaea" and "archaeon" refer to prokaryotic organisms of the domain Bacteria and Archaea in the three-domain system (see Woese C R, et al., Proc Natl Acad Sci USA 1990, 87: 4576-79).

The term "genus" is defined as a taxonomic group of related species according to the Taxonomic Outline of Bacteria and Archaea (Garrity et al. (2007) The Taxonomic Outline of Bacteria and Archaea. TOBA Release 7.7, March 2007. Michigan State University Board of Trustees).

The term "species" is defined as collection of closely related organisms with greater than 97% 16S ribosomal RNA sequence homology and greater than 70% genomic hybridization and sufficiently different from all other organisms so as to be recognized as a distinct unit (e.g., an operational taxonomic unit).

The term "strain" as used herein in reference to a microorganism describes an isolate of a microorganism considered to be of the same species but with a unique genome and, if nucleotide changes are non-synonymous, a unique proteome differing from other strains of the same organism. Strains may differ in their non-chromosomal genetic complement. Typically, strains are the result of isolation from a different host or at a different location and time, but multiple strains of the same organism may be isolated from the same host.

As used herein, the term "microbiota" or "microbiota" refers to an assemblage of microorganisms localized to a distinct environment. Microbiota may include, for example, populations of various bacteria, eukaryotes (e.g., fungi), and/or archaea that inhabit a particular environment. For example, "gut microbiota," "vaginal microbiota," and "oral microbiota" refer to an assemblage of one or more species of microorganisms that are localized to, or found in, the gut, vagina, or mouth, respectively.

"Normal microbiota" refers to a population of microorganisms that localize in a particular environment in a normal, non-pathological state (e.g., a sample of gut microbiota from a subject without enteric infection). A "normal microbiota" has normal membership and normal relative abundance.

"Abnormal microbiota" refers to a population of various microorganisms that localize in a particular environment that differs from the normal microbiota in terms of identity (e.g., membership), absolute amount, or relative amount (e.g., relative abundance) of the various microbes.

"Pathologic microbiota" refers to a population of various microorganisms that localize in a particular environment in a pathological state and that differs from the normal microbiota in terms of identity (e.g., membership), absolute amount, or relative amount (e.g., relative abundance) of the various microbes.

As used herein, the term "commensal microbe" refers to a microorganism that is non-pathogenic to a host and is part of the normal microbiota of the host.

As used herein, the terms "microbial agent," "commensal microbial agent," and "probiotic" refer to compositions comprising a microbe or population of multiple different microbes for administration to a subject.

The terms "pathogen" and "pathogenic" in reference to a microorganism includes any such microorganism that is capable of causing or affecting a disease, disorder or condition of a host containing the microorganism.

As used herein, the terms "antibiotic" and "antibacterial agent" refer to a chemical agent which is active against bacteria. In common usage, an antibiotic is a substance or compound (also called chemotherapeutic agent) that kills or inhibits the growth of bacteria. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (e.g., penicillins, cephalosporins, cephems), or cell membrane (e.g., polymixins), or interfere with essential bacterial enzymes (e.g., quinolones, sulfonamides) usually are bactericidal in nature. Those which target protein synthesis such as the aminoglycosides, macrolides and tetracyclines are usually bacteriostatic. Three newer classes of antibiotics include: cyclic lipopeptides (e.g., daptomycin), glycylcyclines (e.g., tigecycline), and oxazolidinones (e.g., linezolid). Tigecycline is a broad-spectrum antibiotic, while the two others are useful for Gram-positive infections.

The term "mutation" as used herein indicates any modification of a nucleic acid that results in an altered nucleic acid, e.g., that produces an amino acid "substitution" in a polypeptide (e.g., thus producing a "mutant" polypeptide or "mutant" nucleic acid). Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial mutation pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (e.g., a metabolite) between the same substrate and metabolite end product.

A "facultative anaerobic organism" or a "facultative anaerobic microorganism" is defined as an organism that can grow in either the presence or in the absence of oxygen.

A "strictly anaerobic organism" or a "strictly anaerobic microorganism" is defined as an organism that cannot grow in the presence of oxygen and which does not survive exposure to any concentration of oxygen.

An "anaerobic organism" or an "anaerobic microorganism" is defined as an organism that cannot grow in the presence of oxygen.

"Aerobic conditions" are defined as conditions under which the oxygen concentration in the fermentation medium is sufficiently high for an aerobic or facultative anaerobic microorganism to use as a terminal electron acceptor.

In contrast, "anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor. "Anaerobic conditions" are further defined as conditions under which no or small amounts of oxygen are added to the medium at rates of <3 mmol/L/h, preferably <2.5 mmol/L/h, more preferably <2 mmol/L/h and most preferably <1.5 mmol/L/h. "Anaerobic conditions" means in particular completely oxygen-free (e.g., 0 mmol/L/h oxygen) or with small amounts of oxygen added to the medium at rates of, e.g., <0.5 to <1 mmol/L/h.

As used herein, the term "taxonomic unit" is a group of organisms that are considered similar enough to be treated as a separate unit. A taxonomic unit may comprise, e.g., a class, family, genus, species, or population within a species (e.g., strain), but is not limited as such.

As used herein, the terms "operation taxonomic unit," "OTU," and "taxon" are used interchangeably to refer to a group of microorganisms considered similar enough to be treated as a separate unit. In one embodiment, an OTU is a group tentatively assumed to be a valid taxon for purposes of phylogenetic analysis. In another embodiment, an OTU is any of the extant taxonomic units under study. In yet another embodiment, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, a species, a subspecies, a strain, etc. In some embodiments, OTUs can represent one or more organisms from the domains Bacteria, Archaea, or Eukarya at any level of a hierarchal order. In some embodiments, an OTU represents a prokaryotic or fungal order. In some embodiments, an OTU is defined based on extent of homology between biomolecular (e.g., nucleic acid, polypeptide) sequences (e.g., percent identity). For example, in certain cases, the OTU may include a group of microorganisms treated as a unit based on, e.g., a sequence identity of ≥95%, ≥90%, ≥80%, or ≥70% among at least a portion of a differentiating biomarker, e.g., a biomolecule such as the 16S rRNA gene.

As used herein, a biomolecule (e.g., a nucleic acid or polypeptide) has "homology" or is "homologous" to a second biomolecule if the biomolecule sequence has a similar sequence to the second biomolecule sequence. The terms "identity," "percent sequence identity" or "identical" in the context of nucleic acid or polypeptide sequences refer to the residues (nucleotide bases or amino acids) in the two sequences that are the same when aligned for maximum correspondence. There are a number of different algorithms known in the art that can be used to measure sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% 99%, 99.5% or 100% of the nucleotide bases, as measured by any well-known algorithm of sequence identity, such as FASTA, BLAST or Gap, as discussed above.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

As used herein, the term "relative abundance" relates to the abundance of microorganisms of a particular taxonomic unit or OTU in a test biological sample compared to the abundance of microorganisms of the corresponding taxonomic unit or OTU in one or more non-diseased control samples. The "relative abundance" may be reflected in e.g., the number of isolated species corresponding to a taxonomic unit or OTU or the degree to which a biomarker specific for the taxonomic unit or OTU is present or expressed in a given sample. The relative abundance of a particular taxonomic unit or OTU in a sample can be determined using culture-based methods or non-culture-based methods well known in the art. Non-culture based methods include sequence analysis of amplified polynucleotides specific for a taxonomic unit or OTU or a comparison of proteomics-based profiles in a sample reflecting the number and degree of polypeptide-based, lipid-based, polyssacharide-based or carbohydrate-based biomarkers characteristic of one or more taxonomic units or OTUs present in the samples. Relative abundance or abundance of a taxon or OTU can be calculated with reference to all taxa/OTUs detected, or with reference to some set of invariant taxa/OTUs.

Methods for profiling the relative abundances of microbial taxa in biological samples, including biological samples of gut microbiota, are well known in the art. Suitable methods may be sequencing-based or array-based. An exemplary method is detailed in the Experimental section below. Briefly, the microbial component of a gut microbiota sample is characterized by sequencing a nucleic acid suitable for taxonomic classification and assigning the sequencing reads to operational taxonomic units (OTUs) with a defined (e.g., >97%) nucleotide sequence identity to a database of annotated and representative sequences. An example of such a database is Greengenes version of May 2013; however any suitable database may be used. After OTUs are defined, a representative sequence from each OTU can be selected and compared to a reference set. If a match is identified in the reference set, that OTU can be given an identity. Relative abundance of a bacterial taxon may be defined by the number of sequencing reads that can be unambiguously assigned to each taxon after adjusting for genome uniqueness.

In some embodiments, a suitable nucleic acid for taxonomic classification is universally distributed among the gut microbial population being queried allowing for the analysis of phylogenetic relationships among distant taxa, and has both a conserved region and at least one region subject to variation. The presence of at least one variable region allows sufficient diversification to provide a tool for classification, while the presence of conserved regions enables the design of suitable primers for amplification (if needed) and/or probes for hybridization for various taxa at different taxonomic levels ranging from individual strains to whole phyla. While any suitable nucleic acid known in the art may be used, one skilled in the art will appreciate that selection of a nucleic acid or region of a nucleic acid to amplify may differ by environment. In some embodiments, a nucleic acid queried is a small subunit ribosomal RNA gene. For bacterial and archaeal populations, at least the V1, V2, V3, V4, V5, V6, V7, V8, and/or V9 regions of the 16S rRNA gene are suitable, though other suitable regions are known in the art. Guidance for selecting a suitable 16S rRNA region to amplify can be found throughout the art, including Guo et al. PLOS One 8(10) e76185, 2013; Soergel D A W et al. ISME Journal 6: 1440, 2012; and Hamady M et al. Genome Res. 19:1 141, 2009, each hereby incorporated by reference in its entirety.

As used herein, the term "Clostridia" refers to a polyphyletic class of Firmicutes, including *Clostridium* and other similar genera. Clostridia are obligate anaerobes and are often but not always Gram-positive; some Clostridia form spores. In some embodiments, the term "Clostridia" refers to organisms in the taxonomic order Clostridiales.

DETAILED DESCRIPTION

Provided herein are compositions and methods for the inhibition of enteric infection. In particular, compositions comprising bacteria of the class Clostridia are administered to human and/or animal subjects to prevent or decrease susceptibility to enteric infection.

The high susceptibility of neonates to infections has been assumed to be due to immaturity of the immune system, but the mechanism remains unclear. In experiments conducted during development of embodiments herein, by colonizing adult germ-free mice with the cecal contents of neonatal and adult mice, it was demonstrated that the neonatal microbiota is impaired in mediating colonization resistance against two major pathogens causing mortality in neonates. The lack of colonization resistance was caused by the absence of Clostridiales in the neonatal microbiota. Administration of Clostridia, but not *Bacteroides*, restored colonization resistance and abrogated intestinal pathology upon pathogen challenge. Conversely, depletion of Clostridia abolished colonization resistance in adult mice. Furthermore, intragastric administration of Clostridia protected neonatal mice from pathogen infection. The metabolite succinate produced by neonatal bacteria enhanced the ability of these protective Clostridia to colonize the gut. These results demonstrate that the gut microbiota in general, and the presence of Clostridia in particular, is a critical determinant of susceptibility to enteric infection.

In some embodiments, provided herein are methods, kits, and compositions for administering Clostridia bacteria to a subject to promote healthy microbiota and thereby prevent and/or decrease susceptibility to enteric infection/colonization with detrimental or pathogenic microbes (e.g., bacteria).

I. Compositions and Kits

Accordingly, in some embodiments, the present technology provides compositions and kits, e.g., for administration to a subject. In some embodiments, compositions comprise one or more Clostridia species. The present invention is not limited to a particular one or more Clostridia species. Examples include, but are not limited to, those described herein.

In some embodiments, compositions comprise one or more additional components (e.g., including but not limited to, one or more additional additive(s) selected from the group consisting of an energy substrate, a mineral, a vitamin, or combinations thereof). In some embodiments, compositions comprise succinate.

In some embodiments, bacteria are live cells, freeze-dried cells, spores, etc. Freeze-dried bacteria can be stored for several years with maintained viability. In certain applications, freeze-dried bacteria are sensitive to humidity. One way of protecting the bacterial cells is to store them in oil. The freeze dried bacterial cells can be mixed directly with a suitable oil, or alternately the bacterial cell solution can be mixed with an oil and freeze dried together, leaving the bacterial cells completely immersed in oil. Suitable oils may be edible oils such as olive oil, rapeseed oil which is prepared conventionally or cold-pressed, sunflower oil, soy oil, maize oil, cotton-seed oil, peanut oil, sesame oil, cereal germ oil such as wheat germ oil, grape kernel oil, palm oil and palm kernel oil, linseed oil. The viability of freeze-dried bacteria in oil is maintained for at least nine months. Optionally live cells can be added to one of the above oils and stored.

In some embodiments, the compositions are part of a milk replacer (e.g., for administration to a neonatal or young animal). In some embodiments, compositions comprise one or more bacteria as described herein in combination with a milk protein (e.g., caseins or whey proteins).

In some embodiments, compositions are added to nutraceuticals, food products, or foods. In some embodiments, to give the composition or nutraceutical a pleasant taste, flavoring substances such as for example mints, fruit juices, licorice, Stevia rebaudiana, steviosides or other calorie free sweeteners, rebaudioside A, essential oils like *eucalyptus* oil, or menthol can optionally be included in compositions of embodiments of the present invention.

In some composition embodiments, compositions are formulated in pharmaceutical compositions. The bacteria of embodiments of the invention may be administered alone or in combination with pharmaceutically acceptable carriers or diluents, and such administration may be carried out in single or multiple doses as described herein.

Compositions may, for example, be in the form of tablets, resolvable tablets, capsules, bolus, drench, pills sachets, vials, hard or soft capsules, aqueous or oily suspensions, aqueous or oily solutions, emulsions, powders, granules, syrups, elixirs, lozenges, reconstitutable powders, liquid preparations, creams, troches, hard candies, sprays, chewing-gums, creams, salves, jellies, gels, pastes, toothpastes, rinses, dental floss and tooth-picks, liquid aerosols, dry powder formulations, HFA aerosols or organic or inorganic acid addition salts.

The pharmaceutical compositions of embodiments of the invention may be in a form suitable for, e.g., rectal, oral, topical, buccal administration. Depending upon the disorder and patient to be treated and the route of administration, the compositions may be administered at varying doses.

In some embodiments, Clostridia are formulated in pharmaceutical compositions for rectal administration. Such formulations include enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In some embodiments, Clostridia are formulated in pharmaceutical compositions for oral administration. Oral dosage forms include push fit capsules made of gelatin, as well as soft, sealed capsules made of gelatin and a plasticizer, such as glycerol or sorbitol. In specific embodiments, push fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In some embodiments, the bacterial formulation comprises at least $1 \times 10^4$ CFU (e.g., $1 \times 10^4$ CFU, $2 \times 10^4$ CFU, $5 \times 10^4$ CFU, $1 \times 10^5$ CFU, $2 \times 10^5$ CFU, $5 \times 10^5$ CFU, $1 \times 10^6$ CFU, $2 \times 10^6$ CFU, $5 \times 10^6$ CFU, $1 \times 10^7$ CFU, $2 \times 10^7$ CFU, $5 \times 10^7$ CFU, $1 \times 10^8$ CFU, $2 \times 10^8$ CFU, $5 \times 10^8$ CFU, $1 \times 10^9$ CFU, $2 \times 10^9$ CFU, $5 \times 10^9$ CFU, $1 \times 10^{10}$ CFU, $2 \times 10^{10}$ CFU, $5 \times 10^{10}$ CFU, $1 \times 10^{11}$ CFU, $2 \times 10^{11}$ CFU, $5 \times 10^{11}$ CFU, $1 \times 10^{12}$ CFU, $2 \times 10^{12}$ CFU, $5 \times 10^{12}$ CFU, or more or ranges therebetween) of Clostridia bacteria. In some embodiments, the bacterial formulation is administered to the subject in two or more doses (e.g., 2, 3, 4, 5, 6, 7, 8, 9, 10, or more, or ranges therebetween). In some embodiments, the administration of doses are separated by at least 1 day (e.g., 2 days, 3 days, 4 days, 5 days, 6 days, 1 week, 2 weeks, 3 weeks, 4 weeks, or ranges therebetween).

For oral or buccal administration, bacteria of embodiments of the present invention may be combined with various excipients. Solid pharmaceutical preparations for oral administration often include binding agents (for example syrups, acacia, gelatin, tragacanth, polyvinylpyrrolidone, sodium lauryl sulphate, pregelatinized maize starch, hydroxypropyl methylcellulose, starches, modified starches, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone and sodium alginate), disintegrants (such as starch and preferably corn, potato or tapioca starch, alginic acid and certain complex silicates, polyvinylpyrrolidone, gelatin, acacia, sodium starch glycollate, microcrystalline cellulose, crosscarmellose sodium, crospovidone, hydroxypropyl methylcellulose and hydroxypropyl cellulose), lubricating agents (such as magnesium stearate, sodium lauryl sulfate, talc, silica polyethylene glycol waxes, stearic acid, palmitic acid, calcium stearate, carnuba wax, hydrogenated vegetable oils, mineral oils, polyethylene glycols and sodium stearyl fumarate) and fillers (including high molecular weight polyethylene glycols, lactose, calcium phosphate, glycine magnesium stearate, starch, rice flour, chalk, gelatin, microcrystalline cellulose, calcium sulphate, and lactitol). Such preparations may also include preservative agents and antioxidants.

Liquid compositions for oral administration may be in the form of, for example, emulsions, syrups, or elixirs, or may be presented as a dry product for reconstitution with water or other suitable vehicle before use. Such liquid compositions may contain conventional additives such as suspending agents (e.g. syrup, methyl cellulose, hydrogenated edible fats, gelatin, hydroxyalkylcelluloses, carboxymethylcellulose, aluminium stearate gel, hydrogenated edible fats) emulsifying agents (e.g. lecithin, sorbitan monooleate, or acacia), aqueous or non-aqueous vehicles (including edible oils, e.g. almond oil, fractionated coconut oil) oily esters (for example esters of glycerine, propylene glycol, polyethylene glycol or ethyl alcohol), glycerine, water or normal saline; preservatives (e.g. methyl or propyl p-hydroxybenzoate or sorbic acid) and conventional flavouring, preservative, sweetening or colouring agents. Diluents such as water, ethanol, propylene glycol, glycerin and combinations thereof may also be included.

Other suitable fillers, binders, disintegrants, lubricants and additional excipients are well known to a person skilled in the art.

In some embodiments, microbes are spray-dried. In other embodiments, microbes are suspended in an oil phase and are encased by at least one protective layer, which is water-soluble (water-soluble derivatives of cellulose or starch, gums or pectins; See e.g., EP 0 180 743, herein incorporated by reference in its entirety).

In some embodiments, the present technology provides kits, pharmaceutical compositions, or other delivery systems for use in treatment (rehabilitative or prophylactic treatment) of enteric infection (e.g., gastrointestinal infection) in an animal. The kit may include any and all components necessary, useful or sufficient for research or therapeutic uses including, but not limited to, one or more microbes, pharmaceutical carriers, and additional components useful, necessary or sufficient for use in treatment (rehabilitative or prophylactic treatment) of enteric infection (e.g., gastrointestinal infection) in an animal. In some embodiments, the kits provide a sub-set of the required components, wherein it is expected that the user will supply the remaining components. In some embodiments, the kits comprise two or more separate containers wherein each container houses a subset of the components to be delivered.

Optionally, compositions and kits comprise other active components in order to achieve desired therapeutic effects.

Embodiments of the present technology provide compositions comprising microbes (e.g., *Clostridium* species alone or in combination with additional microbes) (e.g., pharmaceutical, nutraceutical, or food compositions) for use in improving or repairing the health of an animal. In some embodiments, compositions find use for use in treatment (rehabilitative or prophylactic treatment) of enteric infection (e.g., gastrointestinal infection) in an animal. In some embodiments, the animal is a domestic or agricultural animal (e.g., cow, sheep, goat, pig, etc.). In some embodiments, the animal is neonatal, newborn, or young. For example, in some embodiments, the animal is one day, 2, days, 3, days, 4 days, 5 days, 6 days, 1 week, 2 weeks, 3 weeks, one month, or 2 months of age, although other ages are specifically contemplated.

In some embodiments, compositions comprising microbes (e.g., Clostridia) are administered once to an animal in need thereof.

In some embodiments, compositions comprise prebiotic compounds such as carbohydrate compounds selected from the group consisting of inulin, fructooligosaccharide (FOS), short-chain fructooligosaccharide (short chain FOS), galacto-oligosaccharide (GOS), xylooligosaccharide (XOS), glangliosides, partially hydrolysed guar gum (PHGG) acacia gum, soybean-gum, apple extract, lactowolfberry, wolfberry extracts or mixture thereof. Other carbohydrates may be present such as a second carbohydrate acting in synergy with the first carbohydrate and that is selected from the group consisting of xylooligosaccharide (XOS), gum, acacia gum, starch, partially hydrolysed guar gum or mixture thereof. The carbohydrate or carbohydrates may be present at about 1 g to 20 g or 1% to 80% or 20% to 60% in the daily doses of the composition. Alternatively, the carbohydrates are present at 10% to 80% of the dry composition.

The daily doses of carbohydrates, and all other compounds administered with the probiotics comply with published safety guidelines and regulatory requirements. This is particularly important with respect to the administration to newborn babies.

In some embodiments, a nutritional composition preferably comprises a source of protein. Dietary protein is preferred as a source of protein. The dietary protein may be any suitable dietary protein, for example animal proteins (such as milk proteins, or meat proteins), vegetable proteins (such as soy proteins, wheat proteins, rice proteins or pea proteins), a mixture of free amino acids, or a combination thereof. Milk proteins such as casein and whey proteins are particularly preferred. The composition may also comprise a source of carbohydrates and/or a source of fat.

In some embodiments, compositions are administered on an ongoing, recurrent, or repeat basis (e.g., multiple times a day, once a day, once every 2, 3, 4, 5, or 6 days, once a week, etc.) for a period of time (e.g., multiple days, months, or weeks). Suitable dosages and dosing schedules are determined by one of skill in the art using suitable methods (e.g., those described in the experimental section below or known to one of skill in the art).

In some embodiments, a single species or strain of Clostridia bacteria is administered. In some embodiments, a formulation of multiple (e.g., 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, or more, or ranges therebetween) Clostridia bacteria species and/or strains are administered.

In some embodiments, Clostridia for administration to a subject are selected from one or more bacteria selected from the class Clostridia.

In some embodiments, one or more bacteria species of the taxonomic order Clostridiales are administered, such as those from the taxonomic families: Caldicoprobacteraceae, Christensenellaceae, Clostridiaceae, Defluviitaleaceae, Eubacteriaceae, Graciibacteraceae, Heliobacteriaceae, Lachnospiraceae, Oscillospiraceae, Peptococcaceae, Peptostreptococcaceae, Ruminococcaceae, Syntrophomonadaceae, and Veillonellaceae.

In some embodiments, one or more bacteria species of the taxonomic family Clostridiaceae are administered, such as those from the taxonomic genera: *Acetanaerobacterium, Acetivibrio, Acidaminobacter, Alkaliphilus, Anaerobacter, Anaerostipes, Anaerotruncus, Anoxynatronum, Bryantella, Butyricicoccus, Caldanaerocella, Caloramator, Caloranaerobacter, Caminicella, Candidatus Arthromitus, Clostridium, Cellulosibacter, Coprobacillus, Dorea, Ethanologenbacterium, Faecalibacterium, Garciella, Guggenheimella, Hespellia, Linmingia, Natronincola, Oxobacter, Parasporobacterium, Sarcina, Soehngenia, Sporobacter, Subdoligranulum, Tepidibacter, Tepidimicrobium, Thermobrachium, Thermohalobacter, Tindallia,* etc.

In some embodiments, one or more bacteria species of the taxonomic genus *Clostridium* are administered, such as those selected form the species of: *Clostridium absonum, Clostridium aceticum, Clostridium acetireducens, Clostridium acetobutylicum, Clostridium acidisoli, Clostridium aciditolerans, Clostridium acidurici, Clostridium aerotolerans, Clostridium aestuarii, Clostridium akagii, Clostridium aldenense, Clostridium aldrichii, Clostridium algidicarni, Clostridium algidixylanolyticum, Clostridium algifaecis, Clostridium algoriphilum, Clostridium alkalicellulosi, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium autoethanogenum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium colletant, Clostridium colicanis, Clostridium colinum, Clostridium collagenovorans, Clostridium cylindrosporum, Clostridium difficile, Clostridium diolis, Clostridium disporicum, Clostridium drakei, Clostridium durum, Clostridium estertheticum, Clostridium estertheticum estertheticum, Clostridium estertheticum laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium*

*gasigenes, Clostridium ghonii, Clostridium glycolicum, Clostridium glycyrrhizinilyticum, Clostridium grantii, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogeniformans, Clostridium hydroxybenzoicum, Clostridium hylemonae, Clostridium jejuense, Clostridium indolis, Clostridium innocuum, Clostridium intestinale, Clostridium irregulare, Clostridium isatidis, Clostridium josui, Clostridium kluyveri, Clostridium lactatifermentans, Clostridium lacusfryxellense, Clostridium laramiense, Clostridium lavalense, Clostridium lentocellum, Clostridium lentoputrescens, Clostridium leptum, Clostridium limosum, Clostridium litorale, Clostridium lituseburense, Clostridium ljungdahlii, Clostridium lortetii, Clostridium lundense, Clostridium magnum, Clostridium malenominatum, Clostridium mangenotii, Clostridium mayombei, Clostridium methoxybenzovorans, Clostridium methylpentosum, Clostridium neopropionicum, Clostridium nexile, Clostridium nitrophenolicum, Clostridium novyi, Clostridium oceanicum, Clostridium orbiscindens, Clostridium oroticum, Clostridium oxalicum, Clostridium papyrosolvens, Clostridium paradoxum, Clostridium paraperfringens (Alias: C. welchii), Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polysaccharolyticum, Clostridium populeti, Clostridium propionicum, Clostridium proteoclasticum, Clostridium proteolyticum, Clostridium psychrophilum, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium scatologenes, Clostridium schirmacherense, Clostridium scindens, Clostridium septicum, Clostridium sordellii, Clostridium sphenoides, Clostridium spiroforme, Clostridium sporogenes, Clostridium sporosphaeroides, Clostridium stercorarium, Clostridium stercorarium leptospartum, Clostridium stercorarium stercorarium, Clostridium stercorarium thermolacticum, Clostridium sticklandii, Clostridium straminisolvens, Clostridium subterminale, Clostridium sufflavum, Clostridium sulfidigenes, Clostridium symbiosum, Clostridium tagluense, Clostridium tepidiprofundi, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium villosum, Clostridium vincentii, Clostridium viride, Clostridium xylanolyticum,* and *Clostridium xylanovorans.*

In some embodiments, the bacteria administered are non-pathogenic. In some embodiments, the bacteria administered are not *C. difficile* or *C. botulinum*.

In some embodiments, the combination of Clostridia strains and/or species is selected to mimic the healthy microbiota of the subject species (e.g., human, chicken, goose, duck, cow, pig, sheep, goat, horse, etc.).

In some embodiments, administration of Clostridia facilitates establishment of beneficial gut microbiota. In some embodiments, administration of Clostridia prevents or decreases susceptibility to infection or colonization by pathogenic or detrimental microbes. For example, in some embodiments, the compositions, methods, kits, etc. herein prevent or decrease susceptibility to infection or colonization by *Clostridium difficile, Salmonella enterica, Bacillus cereus, Helicobacter pylori, Campylobacter,* etc.

In some embodiments, the methods and compositions herein are used to prophylactically prevent infection or colonization with pathogenic or detrimental microbes (e.g., bacteria). In some embodiments, the methods and compositions herein are used to treat infection or colonization with pathogenic or detrimental microbes (e.g., bacteria).

II. Methods of Treatment

In some embodiments, a composition comprising Clostridia is administered to a subject or patient in a pharmaceutically effective amount. In some embodiments, a composition comprising Clostridia, is administered in a therapeutically effective dose.

The dosage amount and frequency are selected to create an effective level of Clostridia without substantially harmful effects. When administered (e.g., orally, rectally, etc.), the dosage will generally comprise at least $1\times10^4$ CFU per dose or per day (e.g., $1\times10^4$ CFU, $2\times10^4$ CFU, $5\times10^4$ CFU, $1\times10^5$ CFU, $2\times10^5$ CFU, $5\times10^5$ CFU, $1\times10^6$ CFU, $2\times10^6$ CFU, $5\times10^6$ CFU, $1\times10^7$ CFU, $2\times10^7$ CFU, $5\times10^7$ CFU, $1\times10^8$ CFU, $2\times10^8$ CFU, $5\times10^8$ CFU, $1\times10^9$ CFU, $2\times10^9$ CFU, $5\times10^9$ CFU, $1\times10^{10}$ CFU, $2\times10^{10}$ CFU, $5\times10^{10}$ CFU, $1\times10^{11}$ CFU, $2\times10^{11}$ CFU, $5\times10^{11}$ CFU, $1\times10^{12}$ CFU, $2\times10^{12}$ CFU, $5\times10^{12}$ CFU per dose or per day, or more per dose or per day, including ranges therebetween) of Clostridia bacteria.

Methods of administering a composition comprising Clostridia (e.g., an effective level of Clostridia) include, without limitation, administration in oral, intranasal, topical, sublingual, rectal, and vaginal forms.

In some embodiments, a single dose of a composition comprising Clostridia (e.g., an effective level of Clostridia) is administered to a subject. In other embodiments, multiple doses are administered over two or more time points, separated by hours, days, weeks, etc. In some embodiments, a composition comprising Clostridia (e.g., an effective level of Clostridia) is administered over a long period of time (e.g., chronically), for example, for a period of months or years (e.g., 1, 2, 3, 4, 5, 6, 7, 8, 9, 10, 11, 12, or more months or years; for the subject's lifetime). In such embodiments, a composition comprising Clostridia (e.g., an effective level of Clostridia) may be taken on a regular scheduled basis (e.g., daily, weekly, etc.) for the duration of the extended period.

The technology also relates to methods of treating a subject with a composition comprising Clostridia (e.g., an effective level of Clostridia). In some embodiments, the subject has a enteric infection (e.g., gastrointestinal infection). In some embodiments, the subject does not have a enteric infection (e.g., gastrointestinal infection) and the composition comprising Clostridia (e.g., an effective level of Clostridia) is administered to prevent a enteric infection (e.g., gastrointestinal infection) or reduce the risk of the subject having a enteric infection (e.g., gastrointestinal infection).

According some embodiments of the technology, a method is provided for treating a subject in need of such treatment with a composition comprising Clostridia (e.g., an effective level of Clostridia). The method involves administering to the subject a composition comprising Clostridia (e.g., an effective level of Clostridia) in any one of the pharmaceutical preparations described above, detailed herein, and/or set forth in the claims. The subject can be any subject in need of such treatment. It should be understood, however, that the composition comprising Clostridia (e.g., an effective level of Clostridia) is a member of a class of compositions and the technology is intended to embrace pharmaceutical preparations, methods, and kits containing related derivatives within this class. Another aspect of the technology then embraces the foregoing summary but read in each aspect as if any such derivative is substituted wherever "composition" appears.

III. Testing

In some embodiments, the present invention provides compositions and methods for research, screening, and diagnostic applications. For example, in some embodiments, diagnostic applications provide a risk or a measure of intestinal health. In some embodiments, the level, presence or absence of Clostridia, is used to provide a diagnosis or prognosis. For example in some embodiments, a lack of or decreased level of Clostridia is associated with an increased risk of decreased gastrointestinal health.

In some embodiments, subjects are tested. Exemplary diagnostic methods are described herein. In some embodiments, intact bacteria are detected (e.g., by detecting surface polypeptides or markers). In other embodiments, bacteria are lysed and nucleic acids or proteins (e.g., corresponding to genes specific to the species of bacteria) are detected.

In some embodiments, bacteria are identified using detection reagents (e.g., a probe, a microarray, e.g., an amplification primer) that specifically interact with a nucleic acid that identifies a particular species of bacteria (e.g., Clostridia).

Some embodiments comprise use of nucleic acid sequencing to identify gut microbiota and/or to detect Clostridia. The term "sequencing," as used herein, refers to a method by which the identity of at least 10 consecutive nucleotides (e.g., the identity of at least 20, at least 50, at least 100, or at least 200 or more consecutive nucleotides) of a polynucleotide are obtained. The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

Some embodiments of the technology comprise acquiring a gut microbiota sample from a subject. As used herein, "gut microbiota sample" refers to a biological sample comprising a plurality of heterogeneous nucleic acids produced by a subject's gut microbiota. Fecal samples are commonly used in the art to sample gut microbiota. Methods for obtaining a fecal sample from a subject are known in the art and include, but are not limited to, rectal swab and stool collection. Suitable fecal samples may be freshly obtained or may have been stored under appropriate temperatures and conditions known in the art. Methods for extracting nucleic acids from a fecal sample are also well known in the art. The extracted nucleic acids may or may not be amplified prior to being used as an input for profiling the relative abundances of bacterial taxa, depending upon the type and sensitivity of the downstream method. When amplification is desired, nucleic acids may be amplified via polymerase chain reaction (PCR). Methods for performing PCR are well known in the art. Selection of nucleic acids or regions of nucleic acids to amplify are discussed above. The nucleic acids comprising the nucleic acid sample may also be fluorescently or chemically labeled, fragmented, or otherwise modified prior to sequencing or hybridization to an array as is routinely performed in the art.

In some embodiments, nucleic acids are amplified using primers that are compatible with use in, e.g., Illumina's reversible terminator method, Roche's pyrosequencing method (454), Life Technologies's sequencing by ligation (the SOLiD platform) or Life Technologies's Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513: 19-39) and Morozova et al (Genomics. 2008 92:255-64), which are incorporated by reference for the general descriptions of the methods and the particular steps of the methods, including all starting products, reagents, and final products for each of the steps.

In another embodiment, the isolated microbial DNA may be sequenced using nanopore sequencing (e.g., as described in Soni et al. Clin Chem 2007 53: 1996-2001, or as described by Oxford Nanopore Technologies). Nanopore sequencing technology is disclosed in U.S. Pat. Nos. 5,795,782, 6,015,714, 6,627,067, 7,238,485 and 7,258,838 and U.S. Pat Appln Nos. 2006003171 and 20090029477.

The isolated microbial fragments may be sequenced directly or, in some embodiments, the isolated microbial fragments may be amplified (e.g., by PCR) to produce amplification products that sequenced. In certain embodiments, amplification products may contain sequences that are compatible with use in, e.g., Illumina's reversible terminator method, Roche's pyrosequencing method (454), Life Technologies's sequencing by ligation (the SOLiD platform) or Life Technologies's Ion Torrent platform, as described above.

In certain embodiments, the sample sequenced may comprise a pool of nucleic acids from a plurality of samples, wherein the nucleic acids in the sample have a molecular barcode to indicate their source. In some embodiments the nucleic acids being analyzed may be derived from a single source (e.g., from different sites or a timecourse in a single subject), whereas in other embodiments, the nucleic acid sample may be a pool of nucleic acids extracted from a plurality of different sources (e.g., a pool of nucleic acids from different subjects), where by "plurality" is meant two or more. Molecular barcodes may allow the sequences from different sources to be distinguished after they are analyzed.

In some embodiments, gut microbiota samples are obtained from a subject (e.g., a healthy subject or a not healthy subject (e.g., a patient or a subject in need of treatment according to the technology provided herein) at any suitable interval of time, varying from minutes to hours apart, days to weeks apart, or even weeks to months apart. Gut microbiota samples may be obtained multiple times a day, week, month or year. The duration of sampling can also vary. For example, the duration of sampling may be for about a month, about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 30 years, or more.

In some embodiments, subjects identified as being at increased risk of decreased intestinal health are administered compositions (e.g., comprising Clostridia) described herein.

In some embodiments, a subject is tested to assess the presence, the absence, or the level of Clostridia in the gut microbiota. In some embodiments, a subject is tested to assess the presence, the absence, or the composition (e.g., membership, relative abundance, etc.) of the gut microbiota. In some embodiments, a subject is tested to assess the presence, the absence, or the level of a pathogenic organism. In some embodiments, a subject is tested to assess the presence, the absence, or the level of a pathogenic organism in the gut microbiota.

Such testing is performed, e.g., by assaying or measuring a biomarker (e.g., a nucleic acid, e.g., a rRNA gene), a metabolite, a physical symptom, an indication, etc.

In some embodiments, a quantitative score is determined, e.g., the relative abundance of Clostridia and/or the relative abundance of a pathogenic organism.

In some embodiments, testing is related to testing for a condition such as enteric infection (e.g., gastrointestinal infection) or risk of enteric infection (e.g., gastrointestinal infection).

In some embodiments, the subject is treated with a composition comprising Clostridia (e.g., an effective level of Clostridia) based on the outcome of the test. Accordingly, in some embodiments, a subject is tested and then treated based on the test results. In some embodiments, a subject is treated and then tested to assess the efficacy of the treatment. In some embodiments, a subsequent treatment is adjusted based on a test result, e.g., the dosage amount, dosage schedule, composition administered, etc. is changed. In some embodiments, a patient is tested, treated, and then tested again to monitor the response to therapy and/or to change the therapy. In some embodiments, cycles of testing and treatment may occur without limitation to the pattern of testing and treating (e.g., test/treat, treat/test, test/treat/test, treat/test/treat, test/treat/test/treat, test/treat/test/treat/test, test/treat/test/test/treat/treat/treat/test, test/treat/treat/test/treat/treat, etc.), the periodicity, or the duration of the interval between each testing and treatment phase.

EXPERIMENTAL

Materials and Methods

Animals. Specific pathogen free (SPF) C57BL/6 mice were originally purchased from Jackson Laboratories. Wild-type, $Myd88^{-/-}/Ticam1^{-/-}$, $Rag1^{-/-}$, and $IL10^{-/-}$ mice on GF background were bred and maintained at the Germ-free Animal Core Facility of the University of Michigan. GF mice were maintained in flexible film isolators and were checked weekly for germ-free status by aerobic and anaerobic culture. The absence of microbiota was verified by microscopic analysis of stained cecal contents to detect unculturable contamination. All animal studies were performed according to approved protocols by the University of Michigan Committee on the Use and Care of Animals.

Reconstitution of GF mice with cecal contents and defined bacteria. Cecal contents from single neonatal and 7-week old SPF mice were diluted into 50 ml (per one adult mouse) or 5 ml (per one 4, 12, 16-day old mouse) of PBS, and passed through a 70 µm cell strainer to eliminate clumps and debris under sterile conditions) under an atmosphere of 5% $H_2$, 5% $CO_2$ and 90% $N_2$ in an anaerobic growth chamber (Coy Manufacturing, Grass Lake, MI). Then 200 µl of the suspension was processed by intragastric gavage into each of the recipient GF mice. *Bacteroides* species were anaerobically grown at 37° C. overnight in pre-reduced chopped-meat broth (Anaerobe systems, Morgan Hill, CA). *E. coli* were grown aerobically overnight in LB broth with shaking.

Enteric pathogen infection. Kanamycin (Km)-resistant and Streptomycin (Sm)-resistant *Salmonella enterica* serovar *Typhimurium* (*S. Typhimurium*) SL1344 ΔspiA was a gift from Dr. Denise Monack, Stanford University. Kanamycin (Km)-resistant wild-type *Citrobacter rodentium* strain DBS120 (pCRP1::Tn5) was a gift from Dr. David Schauer, Massachusetts Institute of Technology. For inoculations, bacteria were grown overnight in LB broth supplemented with Km (50 µg/ml) and Sm (50 µg/ml) for *S. Typhimurium*, and Km (50 µg/ml) for *C. rodentium* with shaking at 37° C. Mice were infected by oral gavage with 0.2 ml of PBS containing approximately $5 \times 10^7$ CFU of *S. Typhimurium*, and $1 \times 10^9$ CFU of *C. rodentium*. Ten-day old mice were left untreated or reconstituted with the 10 mg/ml feces of mice bearing a Clostridia consortium (12) and then infected with *S. Typhimurium* 2 days after the reconstitution. Mouse survival was monitored for 7 days after infection. To determine pathogen loads, fecal pellets and cecal contents were collected from individual mice, homogenized in sterile PBS and plated at serial dilutions onto MacConkey agar plates containing 50 µg/ml Km, and the number of CFU was determined after overnight incubation at 37° C. Mice were sacrificed at one day post-infection (p.i.), and ceca were flushed with PBS and used for colonic cell isolation or fixed in 10% formalin and then processed for H&E staining. Histologic evaluation was performed in a blinded fashion, using a scoring system described previously with some modifications (13). Briefly, a three- to four-point scale was used to denote the severity of inflammation (0, none; 1, mild 2, moderate; and 3, severe), the level of involvement (0, none; 1, mucosa; 2, mucosa and submucosa; and 3, transmural), and extent of epithelial/crypt damage (0, none; 1, basal 1/3; 2, basal 2/3; 3, crypt loss; 4, crypt and surface epithelial destruction). Each variable was then multiplied by a factor reflecting the percentage of the cecum involved (0-25%, 26-50%, 51-75%, and 76-100%), and then summed to obtain the overall score.

Fecal pellet DNA extraction and 16S rRNA gene sequencing and sequence curation. Fecal samples were freshly collected and DNA was extracted using the E.Z.N.A.® stool DNA kit. Amplicons were generated of the V4 region within the 16S rRNA gene and the fragments were sequenced using an Illumina MiSeq (14). These sequences were curated using Mothur (v.1.35) (14, 15) and sequences were binned into operational taxonomic units (OTUs). Taxonomic assignments were determined using a naive Bayesian classifier with the Ribosomal Database Project (RDP) training set (version 10) requiring an 80% bootstrap confidence score (16).

Treatment with vancomycin and SCFAs and special diet. Vancomycin (250 mg/L) was administered in the mouse drinking water for 7 days before *S. Typhimurium* and *C. rodentium* infection and the treatment was kept during the length of the experiment. Succinate (100 mM), Acetate (100 mM), or lactate (50 mM) was administered in the drinking water for 7 days before transfer of fecal microbiota from GF mice reconstituted with Clostridia consortium and the treatment for 14 days. Mice were fed either a conventional PICO LAB rodent diet 5L0D (PMI Nutrition International, LLC), or a customized lactose and cellobiose diet (Harlan TD.130664) in which starch and maltodextrin were replaced with lactose (30% final w/w) and cellobiose (18.9% final w/w), for six weeks prior to oral pathogen challenge.

Quantitative RT-PCR for *Clostridium* cluster IV and XIVa detection. Quantitative real time RT-PCR (qPCR) was performed using a SYBR green PCR master mix and StepOne Real-time PCR system (Applied Biosystems). The amplification program had programmed steps of one cycle at 95° C. for 15 min; followed by 40 cycles of 94° C. for 20 s, 55° C. for 20 s, and 72° C. for 50 s; and finally one cycle at 94° C. for 15 s. The following primer sets were used (17):

*Clostridium* cluster IV
GCACAAGCAGTGGAGT (SEQ ID NO: 1)
CTTCCTCCGTTTTGTCAA (SEQ ID NO: 2)
*Clostridium* cluster XIVa
AAATGACGGTACCTGACTAA (SEQ ID NO: 3)
CTTTGAGTTTCATTCTTGCGAA (SEQ ID NO: 4)

Relative mRNA expression was calculated by the ΔCt method and normalized to the expression of each *Clostridium* cluster of fecal samples from GF mice reconstituted with Clostridia consortium.

CE-TOFMS-based metabolome analysis. Fecal samples were freeze dried and disrupted by vigorous shaking at 1,500 rpm for 10 min with four 3-mm zirconia beads by Shake Master NEO (Bio Medical Science Inc.). 10 mg (±0.5 mg) fecal samples were homogenized with 500 µl MeOH containing internal standards (20 µM each of methionine sulfone, and D-camphor-10-sulfonic acid (CSA)) and 100 mg of 0.1-mm and four of 3-mm zirconia/silica beads (BioSpec Products). After vigorous shaking (1,500 rpm for 5 min) by Shake Master NEO (Bio Medical Science Inc.), 200 µl of Milli-Q water and 500 µl of chloroform was added and then the samples were shaken in the same manner as before. After centrifugation at 4,600×g for 15 min at 4° C., the supernatant was transferred to a 5-kDa cutoff centrifugal filter tube. The filtrate was centrifugally concentrated at 40° C. and reconstituted with 40 µl of Milli-Q water. Ionic metabolites were analyzed using CE-TOFMS in both positive and negative mode (18). All CE-TOFMS experiments were performed using an Agilent CE capillary electrophoresis system (Agilent Technologies, Inc.). To identify peak annotation and quantification, the obtained data were processed using peak analysis software (19).

Statistical analyses. Statistical analyses were performed using GraphPad Prism software version 6.07 (GraphPad Software Inc.). Differences between two groups were evaluated using Student's t test or Mann-Whitney U test. Comparison of more than two groups was performed with one-way ANOVA or two-way repeated measures ANOVA followed by Dunnett's, Bonferroni's, or Sidak's multiple comparisons test. Survival between groups of mice was compared using Log-rank (Mantel-Cox) test. Differences at $P<0.05$ were considered significant.

Results

Figure 1B:
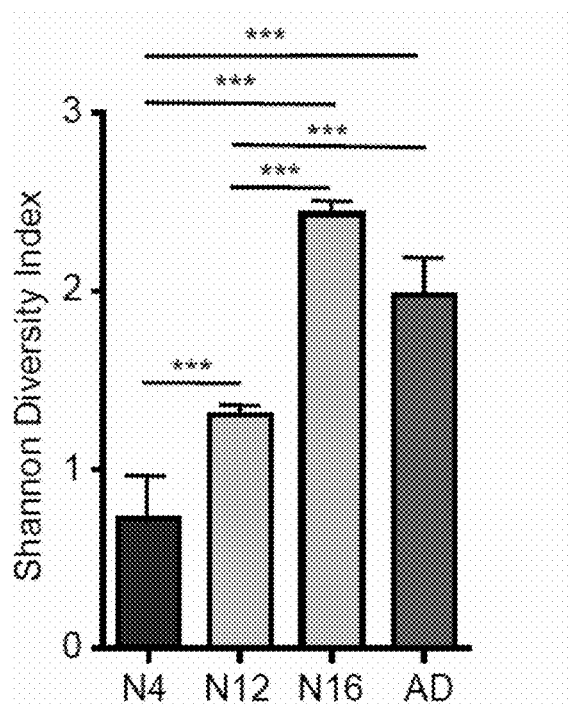
Figure 1C:
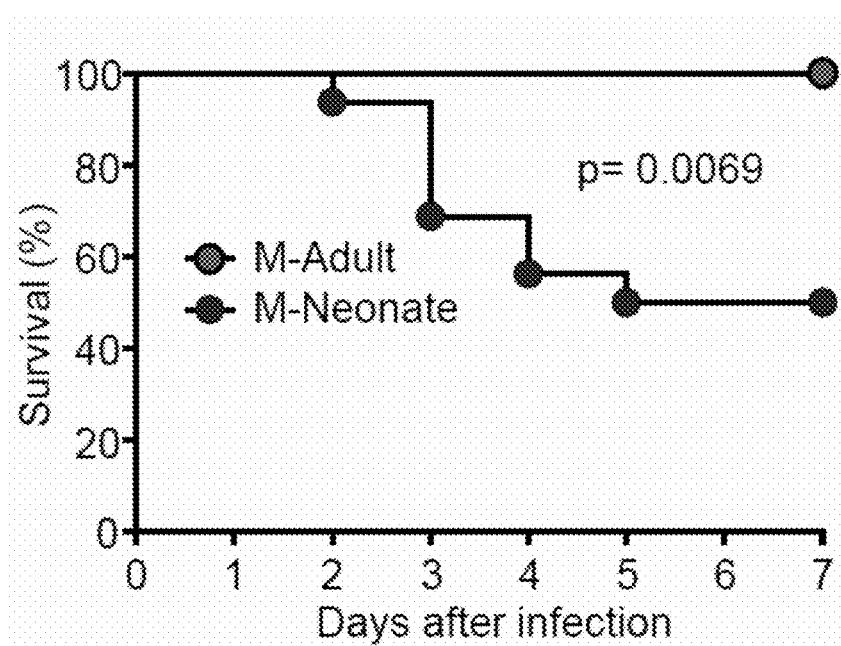
Figure 1D:
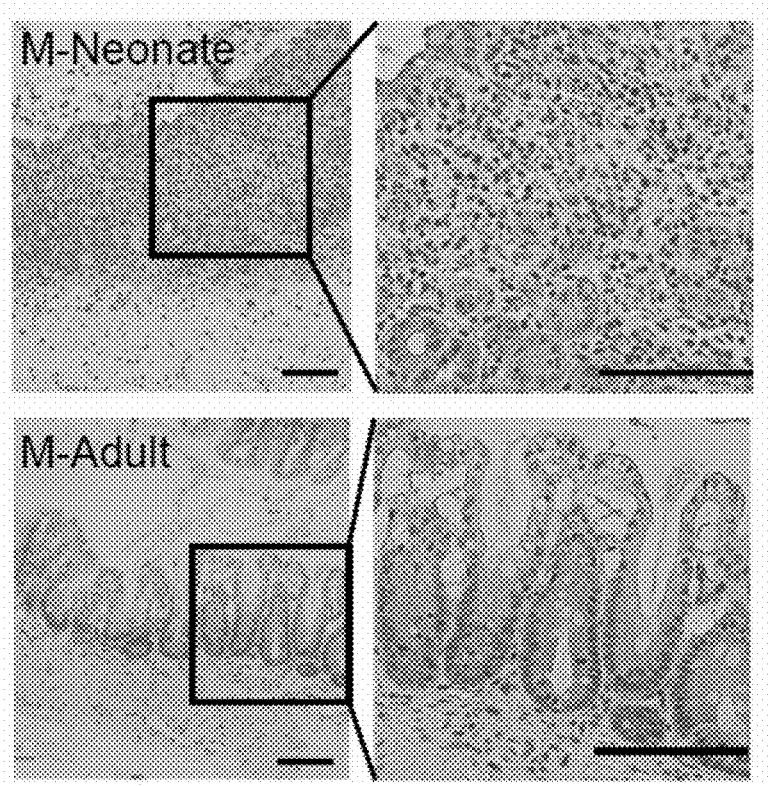
Figure 1E:
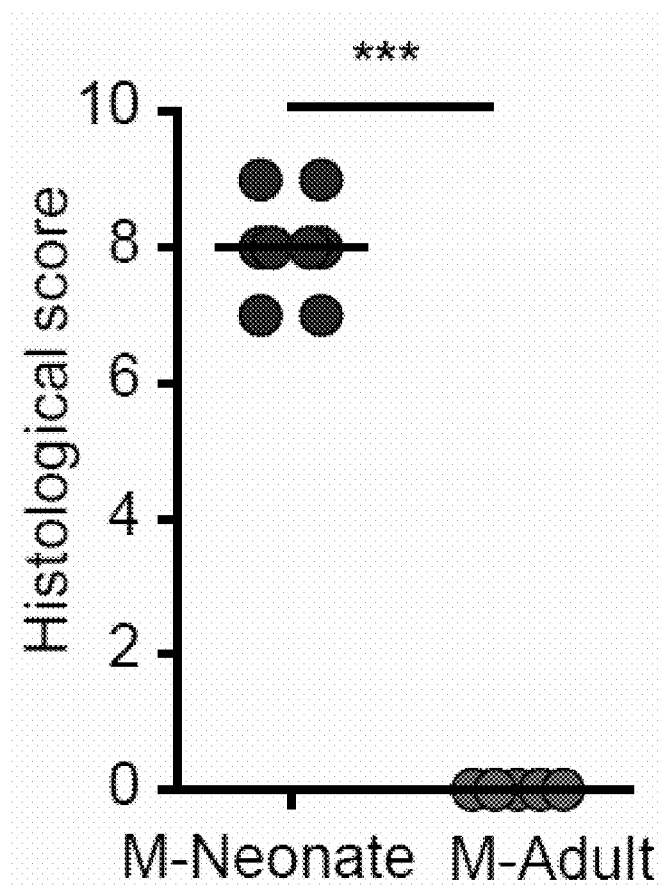
Figure 1G:
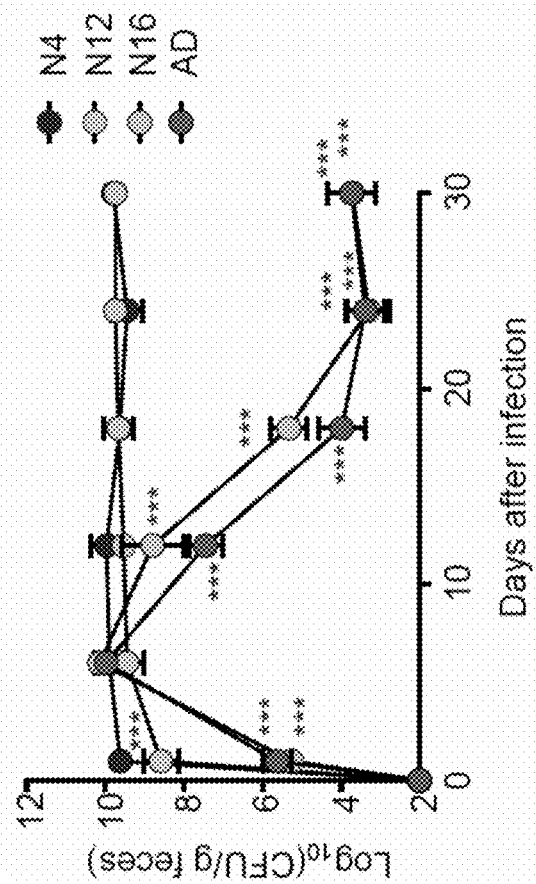
Figure 1F:
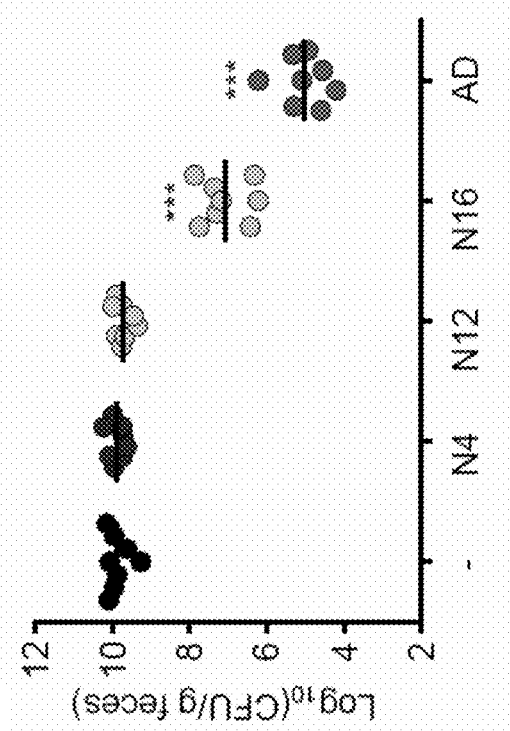
Figure 6:
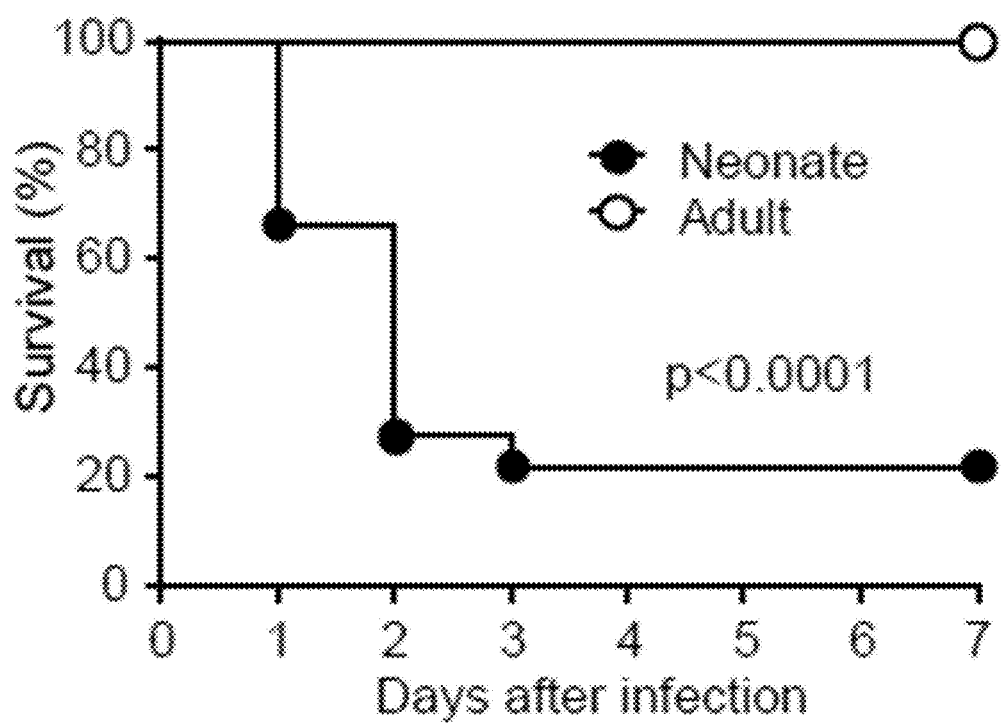
FIG. 6. Neonatal mice are susceptible to oral *Salmonella* infection. Adult (7-week old) and neonate (7-day old) mice were infected with *S. Typhimurium* ΔspiA. Mouse survival is plotted versus time after infection in neonate (n=18) and adult (n=15) mice. P<0.0001 by Log-rank test.

To compare the function of the neonatal and the adult microbiota in colonization resistance against pathogens independently of the age of the host, age-matched adult germ-free (GF) mice were colonized with the cecal contents of neonatal mice or adult mice (7-week old) and the reconstituted mice were kept in isolators to prevent contamination with exogenous bacteria. 16S rRNA gene analysis of the fetal microbiota 21 days after reconstitution revealed that the bacterial composition of adult GF mice colonized with the microbiota from 4-day old mice resembled that of the donor and was dominated by facultative anaerobes including Lactobacillaceae but devoid of Clostridiales and Bacteroidales (FIG. 1A and FIG. 5A). The microbiota of GF mice reconstituted with feces from 12-day old mice was dominated by operational taxonomic units (OTUs) belonging to the Enterobacteriaceae and Lactobacillaceae families and few OTUs belonging to the Lachnospiraceae family compared to that of 16-day old and adult mice (FIGS. 1A-B; FIGS. 5A-B). In contrast, strict anaerobic bacteria with a large number of Clostridiales OTUs belonging to Lachnospiraceae and Ruminococcaceae families as well as Porphyromonadaceae and unclassified Bacteroidales were prevalent in GF mice colonized with the cecal contents of 16-day old or adult mice (FIGS. 1A-B; FIGS. 5A-B). Consistently, there was a greater diversity in the microbiota of GF mice reconstituted with 16-day old and adult mice than in mice colonized with the cecal contents of 4-day and 12-day old mice (FIG. 1B). To assess the ability of the different microbiotas to control pathogen replication in the intestine in the absence of systemic invasion, reconstituted GF mice were intragastrically infected with a *Salmonella enterica* serovar Typhimurium (*S.* Typhimurium) mutant deficient in the type III secretion system (T3SS) encoded by *Salmonella* pathogenicity island-2 (ΔspiA) which replicates normally in the intestine, but is deficient in systemic spread (9, 10). It was found that ~50% of GF mice colonized with the microbiota of 4-day old mice succumbed to *S.* Typhimurium infection whereas all GF mice colonized with the adult microbiota survived (FIG. 1C). The increased mortality of GF mice harboring a microbiota from 4-day old mice was associated with marked intestinal cell damage, submucosa edema and inflammatory cell infiltrates in the cecum which were absent in GF mice colonized with the microbiota of adult mice (FIGS. 1D, E). Consistent with these findings, ~80% of 7-day old mice infected with *S.* Typhimurium ΔspiA succumbed whereas all adult mice survived the infection (FIG. 6). Notably, GF mice colonized with the microbiota from 4- and 12-day old mice harbored ~4-5 logs higher pathogen loads in the feces than mice colonized with the microbiota from 16-day old or adult mice (FIG. 1F). To assess the function of the microbiota in colonization resistance against another enteric pathogen, infected adult GF mice were intragastrically reconstituted with the microbiota of neonatal and adult mice with *Citrobacter rodentium*, a natural pathogen of mice that is used to model human infections with enteropathogenic *E. coli* (ref. 11; incorporated by reference in its entirety). Consistent with the *S.* Typhimurium results, GF mice colonized with microbiota from 4- and 12-day old mice were impaired in resisting colonization of *C. rodentium* as evidenced by 6-logs higher pathogen loads in the feces by day 25-30 post-infection in comparison to mice colonized with the microbiota from 16-day old or adult mice (FIG. 1G). These results demonstrate that the gut microbiota from neonatal mice is impaired in mediating colonization resistance against *S.* Typhimurium and *C. rodentium*.

Figure 2A:
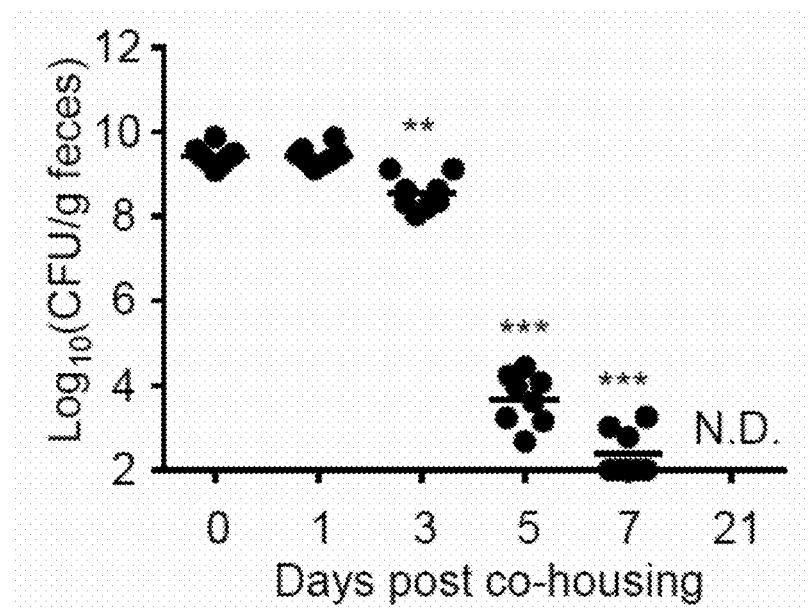
FIGS. 2A-E. Depletion of Clostridiales and Bacteroidales abolishes colonization resistance against bacterial pathogens in adult mice.
Figure 2B:
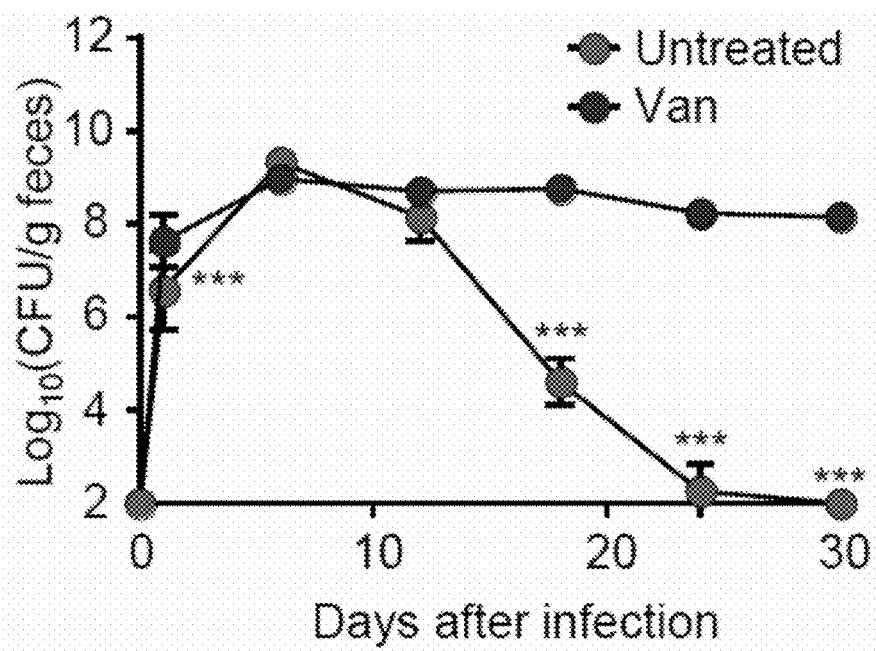
Figure 2C:
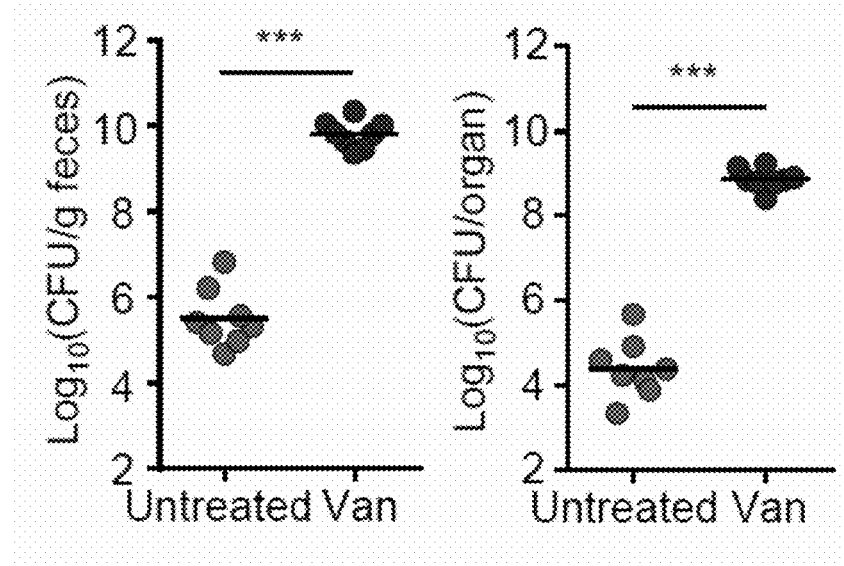
Figure 2D:
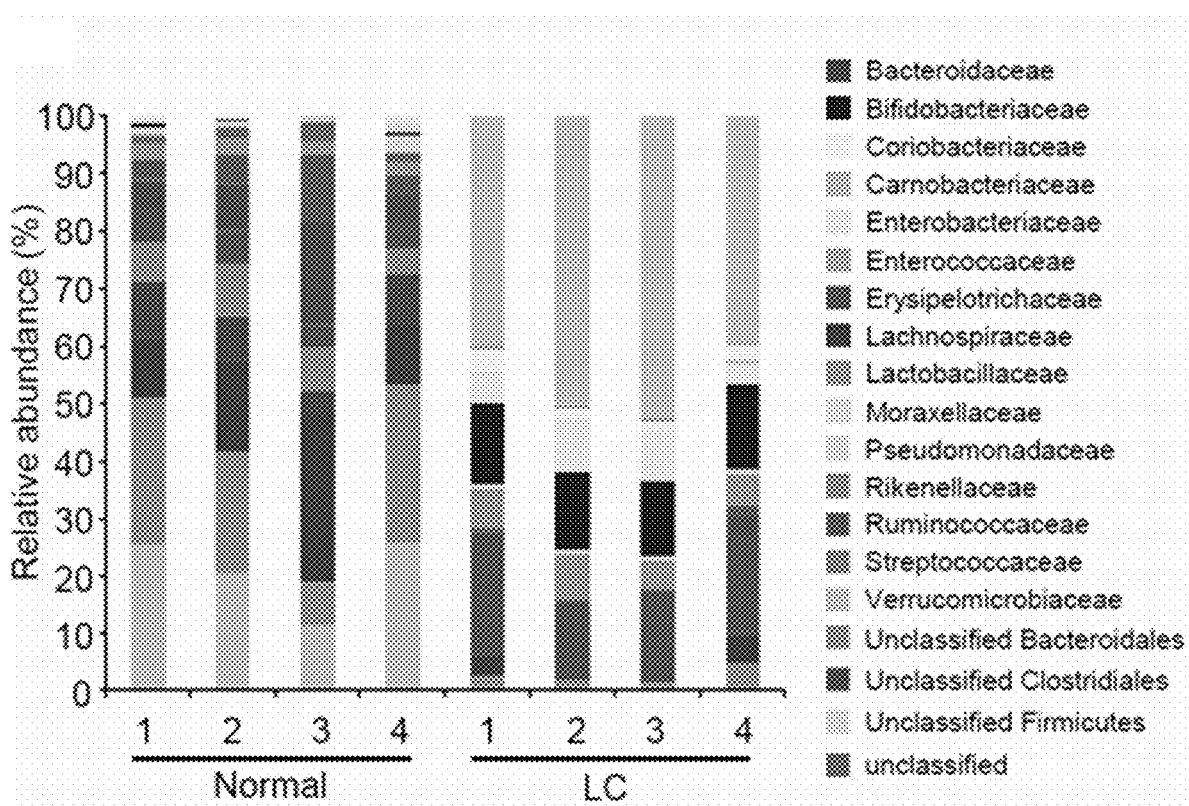
Figure 2E:
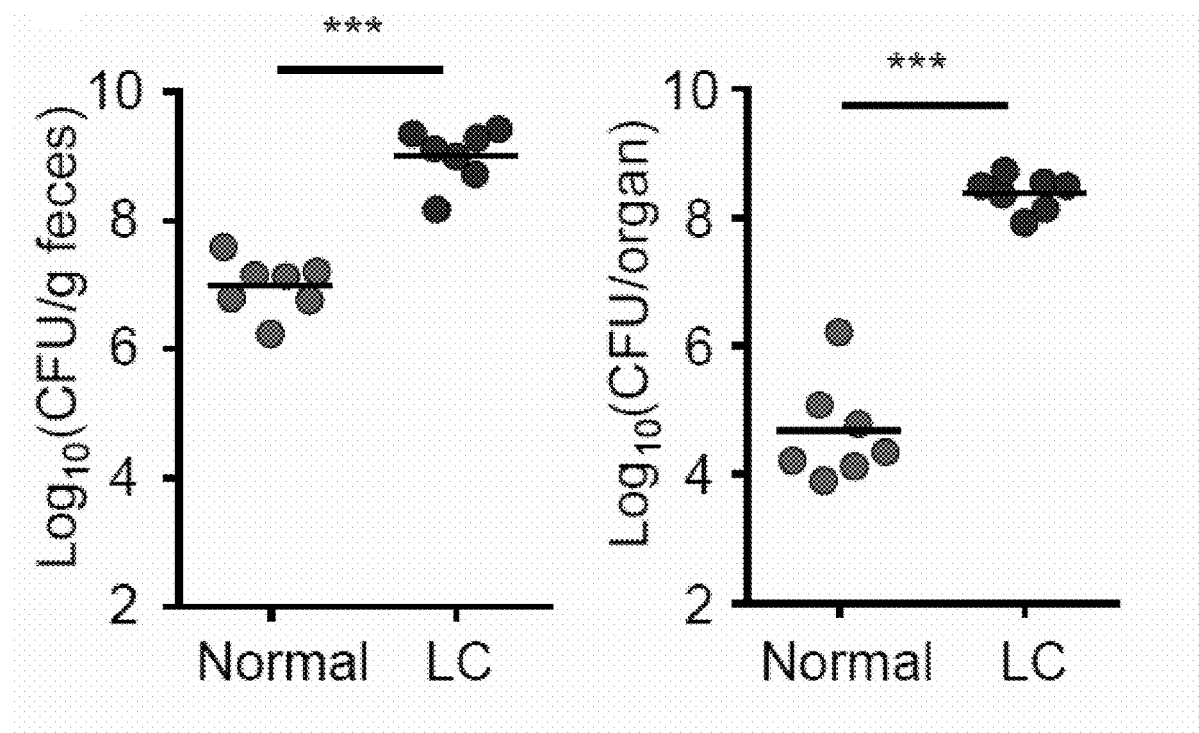
Figure 7:
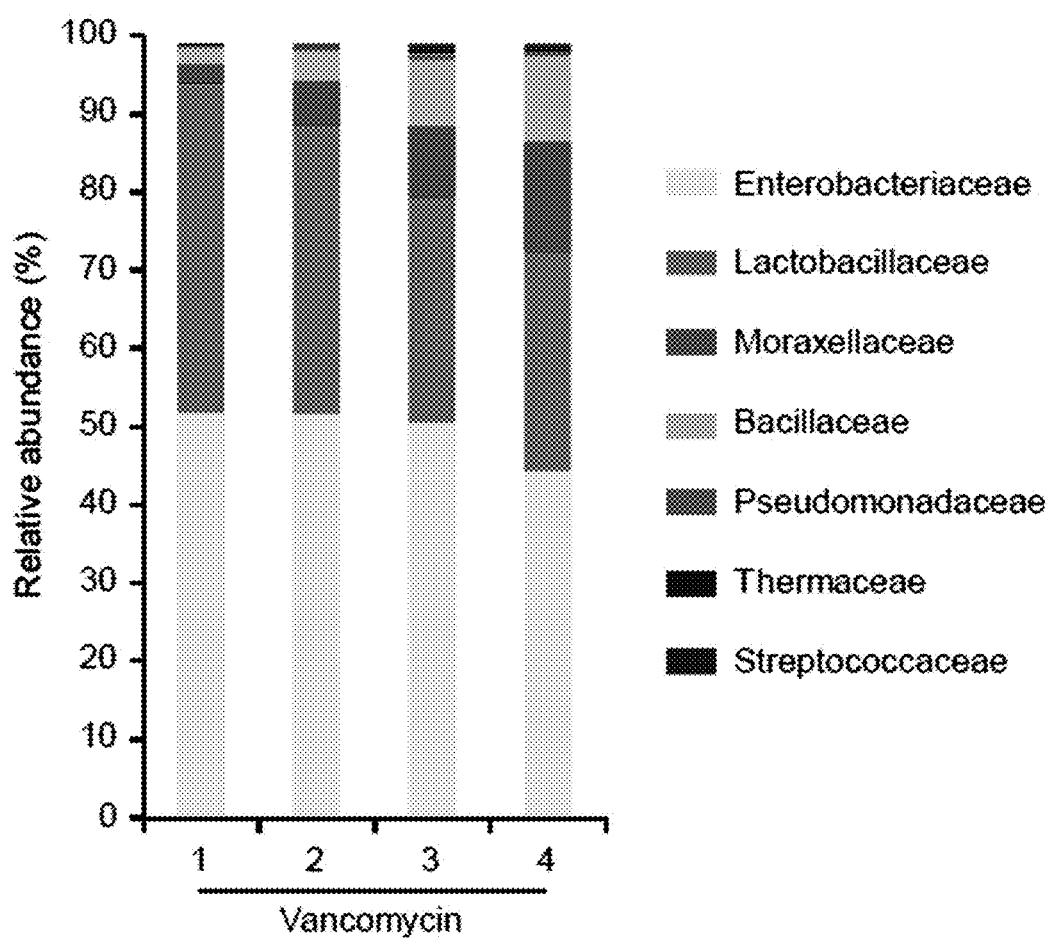
FIG. 7. Vancomycin treatment depleted the microbiota of Clostridiales and Bacteroidales and increased the abundance of Enterobacteriaceae and Lactobacillaceae. Bars show the relative abundance of operational taxonomic units (OTUs) from families in fecal samples from vancomycin-treated mice. Colors correspond to families.

Experiments were conducted during development of embodiments herein to determine whether the adult microbiota can restore colonization resistance to mice harboring a neonatal microbiota. To assess this, GF mice colonized with the microbiota of 4-day old mice were orally infected with *C. rodentium* and on day 30 post-infection the adult microbiota was transferred to infected mice by cohousing. Notably, the burden of *C. rodentium* in GF mice harboring the day 4 neonatal microbiota declined by ~5-logs after 5 days and was further reduced by ~6-logs by day 7 of cohousing with adult mice (FIG. 2A). These findings indicate that addition of symbiotic bacteria present in adult mice to the neonatal microbiota is sufficient to restore colonization resistance. Experiments were conducted during development of embodiments herein to determine whether treatment of adult mice that render the composition of the microbiota comparable to that of neonatal mice affect colonization resistance against pathogens. Accordingly, adult mice were treated with high dose vancomycin, which depleted the microbiota of Clostridiales and Bacteroidales and increased the abundance of Enterobacteriaceae and Lactobacillaceae (FIG. 7). Vancomycin-treated mice exhibited increased pathogen colonization after infection with *C. rodentium* and harbored ~6-logs higher pathogen loads in the feces by day 25-30 after infection when compared to untreated mice (FIG. 2B). Likewise, treatment of adult mice with vancomycin increased *S. Typhimurium* colonization in fecal and cecal contents by 4 to 5-logs (FIG. 2C). In another approach to alter the composition of the adult microbiota, adult mice were fed a lactose and cellobiose-rich diet for 6 weeks and assessed the fecal microbiota by 16S rRNA gene analysis. The composition of the microbiota in mice fed a lactose and cellobiose-rich diet resembled that of 4-day and 12-day old mice in that it was dominated by Erysipelotrichaceae, Enterobacteriaceae, Verrucomicrobiaceae, Lactobacillaceae, and Bifidobacteriaceae and depleted of Clostridiales and Bacteroidales (FIG. 2D). Notably, adult mice fed the lactose and cellobiose-rich diet harbored increased loads of *S. Typhimurium* in fecal and cecal contents when compared to mice fed a conventional chow (FIG. 2E).

The impaired colonization resistance of the neonatal microbiota against enteric pathogens is associated with the absence or reduced numbers of Clostridiales and Bacteroidales compared with the microbiota of 16-day old or adult mice. To determine whether Clostridiales or Bacteroidales species are important in mediating colonization resistance, GF mice harboring the microbiota from 4-day old mice were gavaged with a consortium of 72 mouse Clostridia species (ref. 12; incorporated by reference in its entirety; see Table 1), a mixture of four mouse *Bacteroides* species or left untreated.

TABLE 1

OTUs in fecal samples from GF mice reconstituted with Clostridia consortium

| OTU | Class | Order | Family | Relative abundance |
|---|---|---|---|---|
| Otu00005 | Clostridia | Clostridiales | Lachnospiraceae | 0.24108 |
| Otu00016 | Clostridia | Clostridiales | Ruminococcaceae | 0.09063 |
| Otu00066 | Clostridia | Clostridiales | Ruminococcaceae | 0.06124 |
| Otu00039 | Clostridia | Clostridiales | Ruminococcaceae | 0.05600 |
| Otu00023 | Clostridia | Clostridiales | Lachnospiraceae | 0.04535 |
| Otu00080 | unclassified | unclassified | unclassified | 0.04402 |
| Otu00017 | Clostridia | Clostridiales | Lachnospiraceae | 0.04173 |
| Otu00037 | Clostridia | Clostridiales | Lachnospiraceae | 0.04060 |
| Otu00032 | Clostridia | Clostridiales | Lachnospiraceae | 0.03201 |
| Otu00103 | Clostridia | Clostridiales | unclassified | 0.02749 |
| Otu00049 | Clostridia | Clostridiales | Lachnospiraceae | 0.02624 |
| Otu00046 | Clostridia | Clostridiales | Lachnospiraceae | 0.02346 |
| Otu00090 | Clostridia | Clostridiales | Lachnospiraceae | 0.02262 |
| Otu00069 | Clostridia | Clostridiales | Lachnospiraceae | 0.02221 |
| Otu00019 | Clostridia | Clostridiales | Lachnospiraceae | 0.02072 |
| Otu00013 | Clostridia | Clostridiales | Ruminococcaceae | 0.01996 |
| Otu00035 | Clostridia | Clostridiales | Ruminococcaceae | 0.01641 |
| Otu00057 | Clostridia | Clostridiales | Ruminococcaceae | 0.01326 |
| Otu00027 | Clostridia | Clostridiales | Lachnospiraceae | 0.01105 |
| Otu00102 | Clostridia | Clostridiales | Lachnospiraceae | 0.01004 |
| Otu00055 | Clostridia | Clostridiales | Lachnospiraceae | 0.00976 |
| Otu00106 | Clostridia | Clostridiales | Ruminococcaceae | 0.00943 |
| Otu00222 | Clostridia | Clostridiales | Lachnospiraceae | 0.00927 |
| Otu00198 | Clostridia | Clostridiales | Lachnospiraceae | 0.00766 |
| Otu00041 | Clostridia | Clostridiales | Ruminococcaceae | 0.00750 |
| Otu00122 | Clostridia | Clostridiales | unclassified | 0.00746 |
| Otu00105 | Clostridia | Clostridiales | unclassified | 0.00742 |
| Otu00044 | Clostridia | Clostridiales | Lachnospiraceae | 0.00681 |
| Otu00082 | Clostridia | Clostridiales | unclassified | 0.00568 |
| Otu00058 | Clostridia | Clostridiales | Ruminococcaceae | 0.00472 |
| Otu00131 | Clostridia | Clostridiales | Lachnospiraceae | 0.00387 |
| Otu00074 | Clostridia | Clostridiales | Lachnospiraceae | 0.00379 |
| Otu00070 | Clostridia | Clostridiales | Lachnospiraceae | 0.00355 |
| Otu00078 | Clostridia | Clostridiales | Lachnospiraceae | 0.00355 |
| Otu00126 | Clostridia | Clostridiales | Ruminococcaceae | 0.00331 |
| Otu00095 | Clostridia | Clostridiales | Lachnospiraceae | 0.00278 |
| Otu00079 | Clostridia | Clostridiales | unclassified | 0.00274 |
| Otu00121 | Clostridia | Clostridiales | Lachnospiraceae | 0.00270 |
| Otu00101 | Clostridia | Clostridiales | Lachnospiraceae | 0.00238 |
| Otu00100 | Clostridia | Clostridiales | Lachnospiraceae | 0.00234 |
| Otu00132 | Clostridia | Clostridiales | unclassified | 0.00226 |
| Otu00182 | Clostridia | Clostridiales | Lachnospiraceae | 0.00214 |
| Otu00076 | Clostridia | Clostridiales | Lachnospiraceae | 0.00206 |
| Otu00113 | Clostridia | Clostridiales | Lachnospiraceae | 0.00202 |
| Otu00072 | Clostridia | Clostridiales | Lachnospiraceae | 0.00198 |
| Otu00141 | Clostridia | Clostridiales | Lachnospiraceae | 0.00169 |
| Otu00155 | Clostridia | Clostridiales | Lachnospiraceae | 0.00153 |
| Otu00067 | Clostridia | Clostridiales | Lachnospiraceae | 0.00145 |
| Otu00167 | Clostridia | Clostridiales | Lachnospiraceae | 0.00141 |
| Otu00158 | Clostridia | Clostridiales | unclassified | 0.00141 |
| Otu00124 | Clostridia | Clostridiales | Lachnospiraceae | 0.00093 |
| Otu00200 | Clostridia | Clostridiales | Ruminococcaceae | 0.00089 |
| Otu00168 | Clostridia | Clostridiales | Ruminococcaceae | 0.00077 |
| Otu00054 | Clostridia | Clostridiales | Lachnospiraceae | 0.00069 |
| Otu00181 | Clostridia | Clostridiales | Lachnospiraceae | 0.00056 |
| Otu00207 | Clostridia | Clostridiales | Ruminococcaceae | 0.00048 |
| Otu00235 | unclassified | unclassified | unclassified | 0.00088 |
| Otu00225 | Clostridia | Clostridiales | Lachnospiraceae | 0.00016 |
| Otu00272 | Clostridia | Clostridiales | unclassified | 0.00016 |
| Otu00401 | Clostridia | Clostridiales | Lachnospiraceae | 0.00016 |
| Otu00087 | Clostridia | Clostridiales | Lachnospiraceae | 0.00012 |
| Otu00441 | unclassified | unclassified | unclassified | 0.00038 |
| Otu00221 | Clostridia | Clostridiales | Lachnospiraceae | 0.00008 |
| Otu00202 | Clostridia | Clostridiales | Lachnospiraceae | 0.00004 |
| Otu00515 | Clostridia | Clostridiales | Lachnospiraceae | 0.00004 |
| Otu00511 | Clostridia | Clostridiales | unclassified | 0.00004 |
| Otu00606 | Clostridia | unclassified | unclassified | 0.00004 |
| Otu00514 | Clostridia | Clostridiales | Lachnospiraceae | 0.00004 |
| Otu00984 | Clostridia | Clostridiales | Lachnospiraceae | 0.00004 |
| Otu01032 | Clostridia | Clostridiales | unclassified | 0.00004 |
| Otu01087 | Clostridia | Clostridiales | Lachnospiraceae | 0.00004 |
| Otu01088 | Clostridia | Clostridiales | Ruminococcaceae | 0.00004 |

Figure 3A:
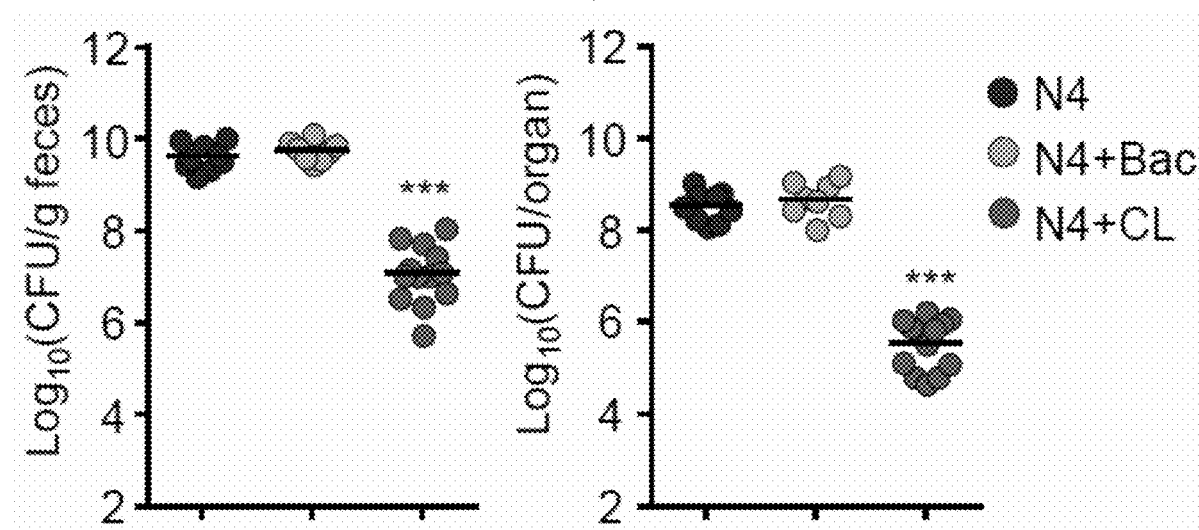
FIGS. 3A-G. Administration of Clostridia, but not *Bacteroides*, restores colonization resistance against bacterial pathogens in the gut.
Figure 3B:
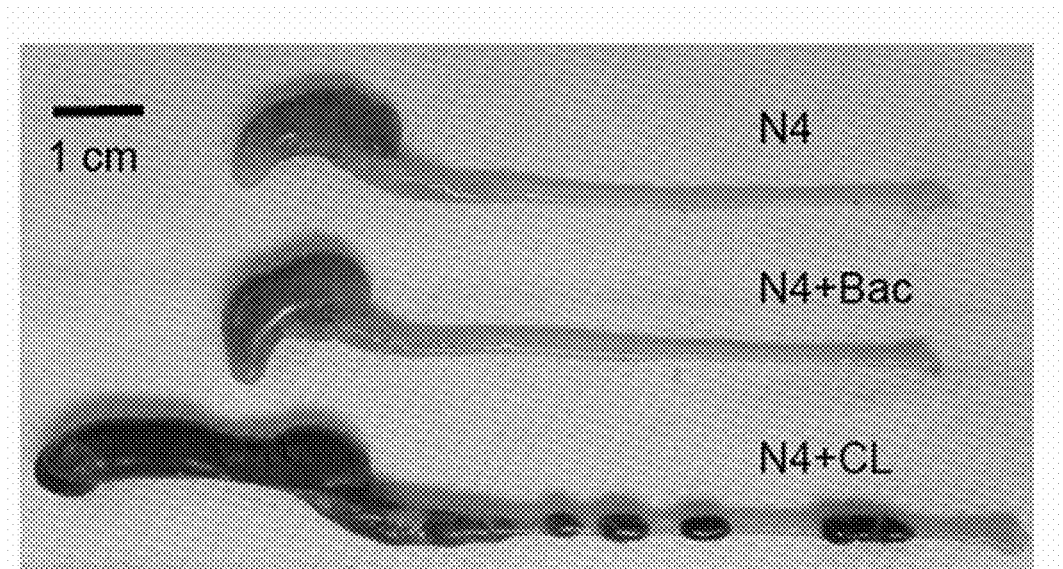
Figure 3C:
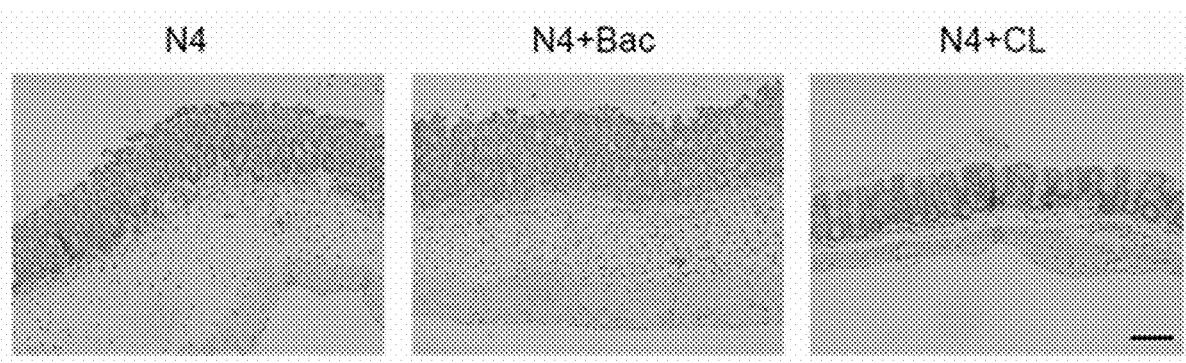
Figure 3D:
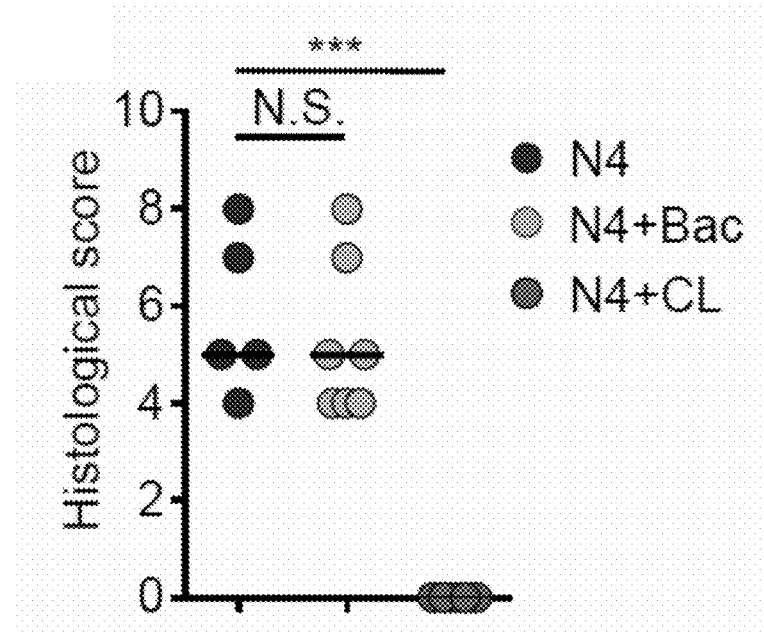
Figure 3E:
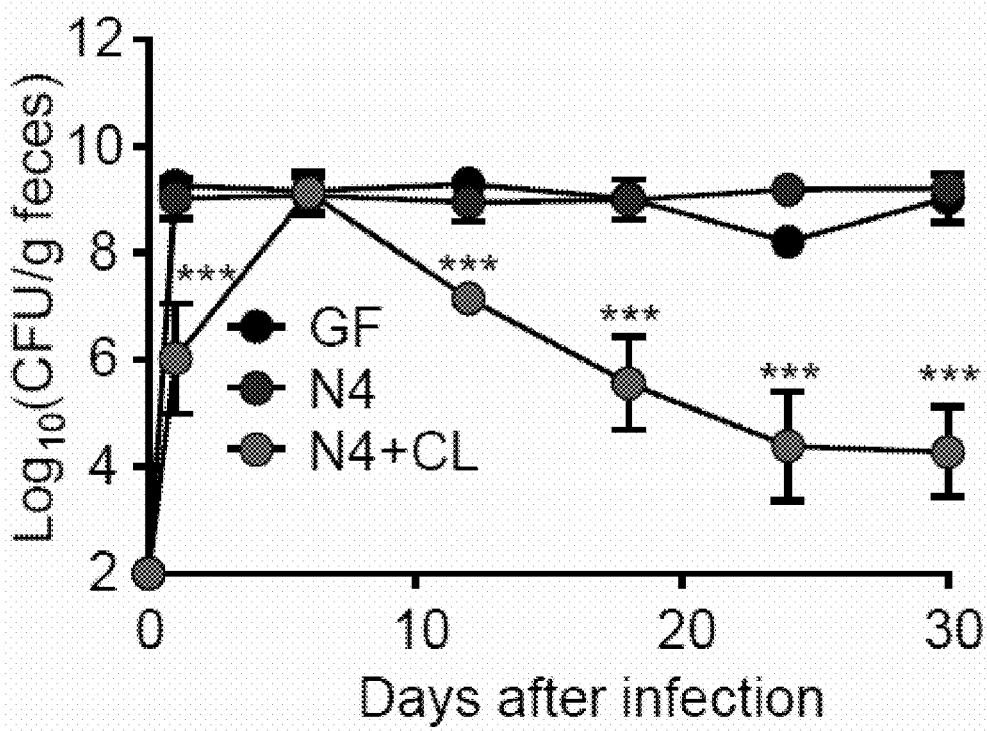
Figure 3F:
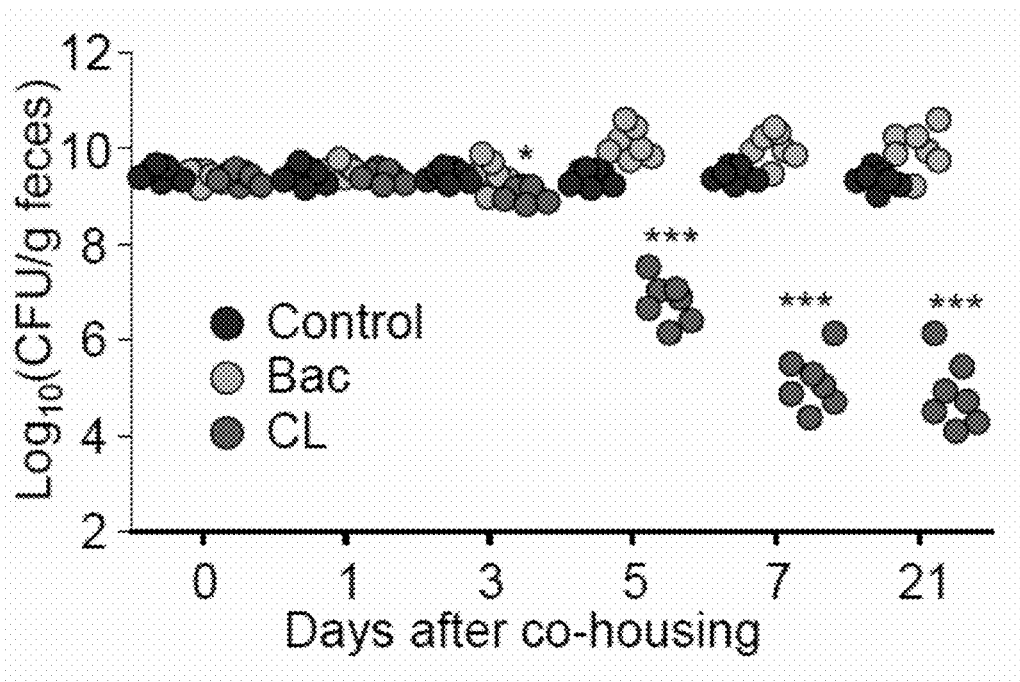
Figure 3G:
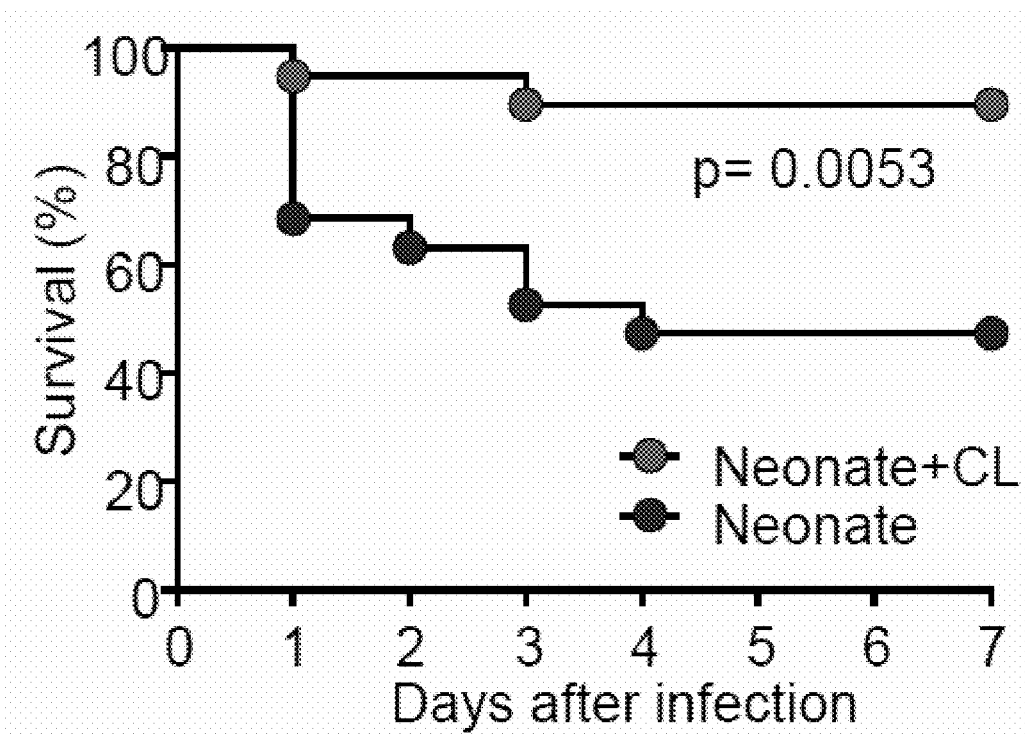
Figure 8:
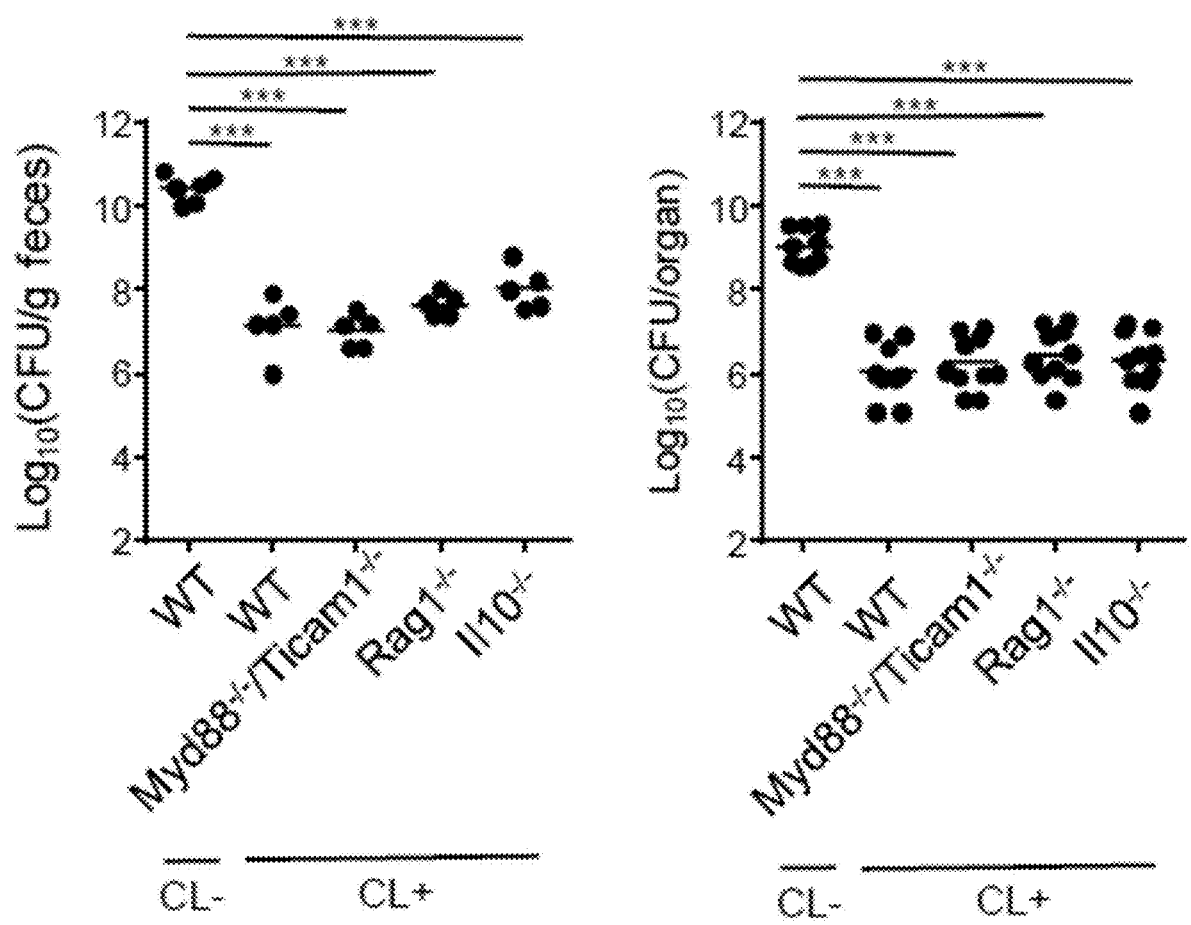
FIG. 8. Clostridiales-mediated colonization resistance against *Salmonella* in the intestine does not require host stimulation via innate MyD88/Trif-regulated pathways or adaptive immunity. Wild-type (WT) GF mice reconstituted with cecal content of 4-day old mice (CL−) or WT, Myd88$^{-/-}$ Trif$^{-/-}$, Rag1$^{-/-}$, or IL10$^{-/-}$ mice were reconstituted with cecal content of 4-day old mice plus Clostridia consortium (CL+). Reconstituted mice were infected with *S. Typhimurium* ΔspiA. Pathogen loads (CFU/gram) in fecal and cecal contents were determined on day 1 after infection. ***; P<0.001, Dunnett's multiple comparisons test.

Notably, administration of Clostridia, but not *Bacteroides* species, restored colonization resistance in the neonatal microbiota against *S. Typhimurium* as determined by analysis of pathogen loads in fecal or cecal contents (FIG. 3A). The reduced pathogen loads elicited by Clostridia administration were associated with an increase in the length of the cecum and colon, a marker of diminished intestinal inflammation, when compared to untreated mice or mice gavaged with *Bacteroides* (FIG. 3B). Consistently, *S. Typhimurium* infection induced robust epithelial damage, submucosal edema and an inflammatory cell infiltrate in GF mice harboring the microbiota from 4-day old mice in the absence and presence of *Bacteroides* species (FIGS. 3C and D). *S. Typhimurium* infection did not induce any detectable epithelial damage or inflammatory pathology in GF mice colonized with the microbiota from 4-day old mice and gavaged with Clostridia (FIGS. 3C and D). Experiments were conducted during development of embodiments herein to determine whether host immunity plays a role in Clostridia-mediated colonization resistance against *S. Typhimurium* infection in the intestine. The microbiota from 4-day old mice was transferred to GF mice deficient in Myd88/Trif, two essential adaptors for signaling via the Toll-like/IL-1/IL-18 receptor family, Rag-1 devoid of B and T cells or the cytokine IL-10. All of these reconstituted mutant GF mice exhibited unimpaired colonization resistance against *S. Typhimurium* infection upon intragastric administration of Clostridia compared to GF mice that were not gavaged with Clostridia (FIG. 8). Thus, colonization resistance against *S. Typhimurium* in the intestine does not require host stimulation via innate MyD88/Trif-regulated pathways or adaptive immunity. Similar to that observed with *S. Typhimurium*, the pathogen loads in the feces of GF mice or GF previously reconstituted with the microbiota of 4-day old mice and then orally infected with *C. rodentium* were reduced by 4 to 5-logs after administration of Clostridia, but not with a mixture of four *Bacteroides* species (FIGS. 3E and 3F). To determine whether Clostridia administration protected neonatal mice from pathogen challenge, 10-day old mice were gavaged with the Clostridia consortium or left untreated and then intragastrically infected with the *S. Typhimurium* ΔspiA mutant. Notably, ~50% of the neonatal mice inoculated with *S. Typhimurium* succumbed to infection whereas >90% of the neonatal mice previously gavaged with Clostridia survived (FIG. 3G). Collectively, these results indicate that Clostridia specifically mediate colonization resistance against *S. typhimurium* and *C. rodentium*. Furthermore, administration of Clostridia protects neonatal mice from mortality induced by pathogen challenge.

Figure 4A:
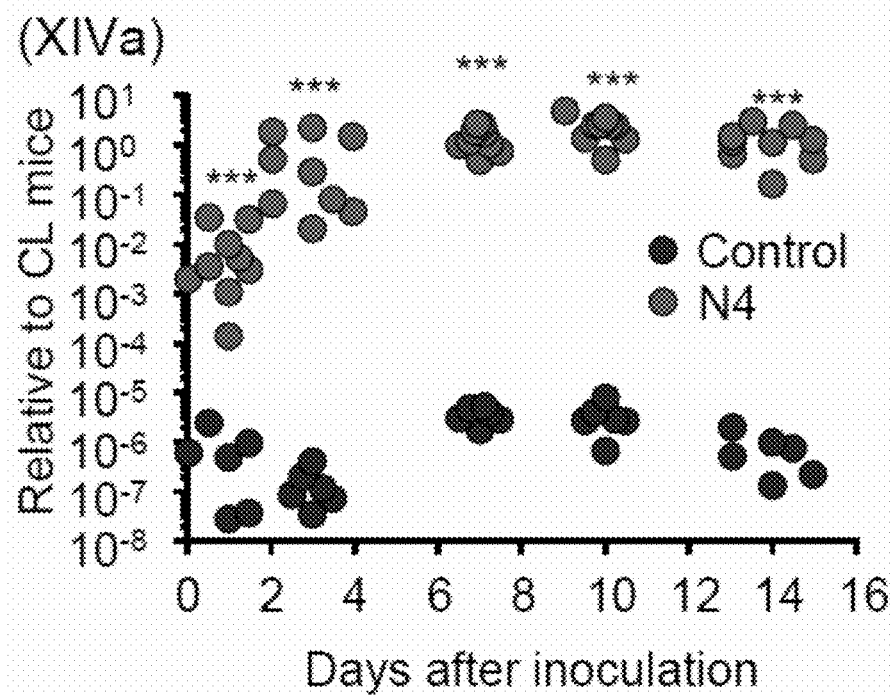
Figure 4B:
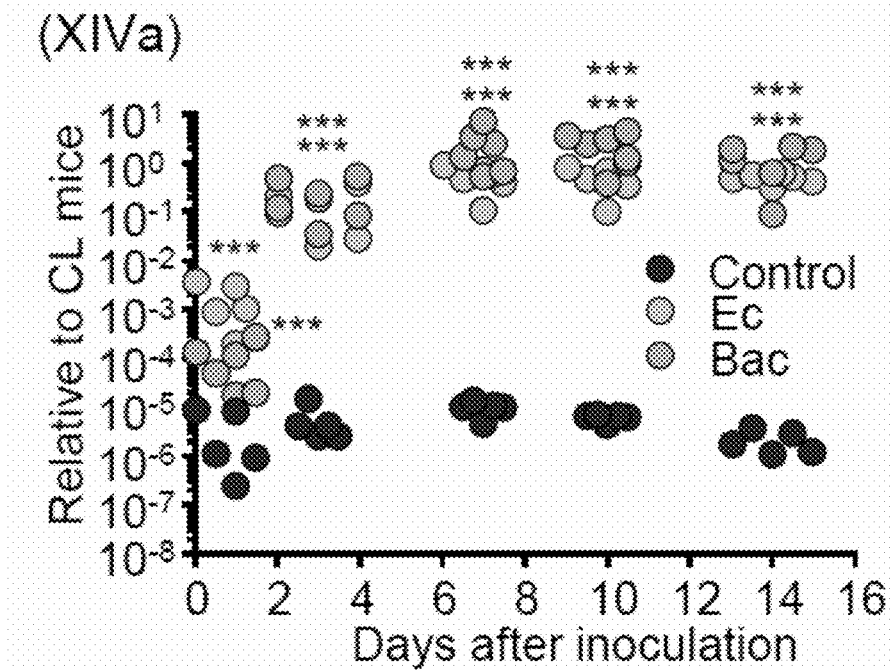
Figure 4D:
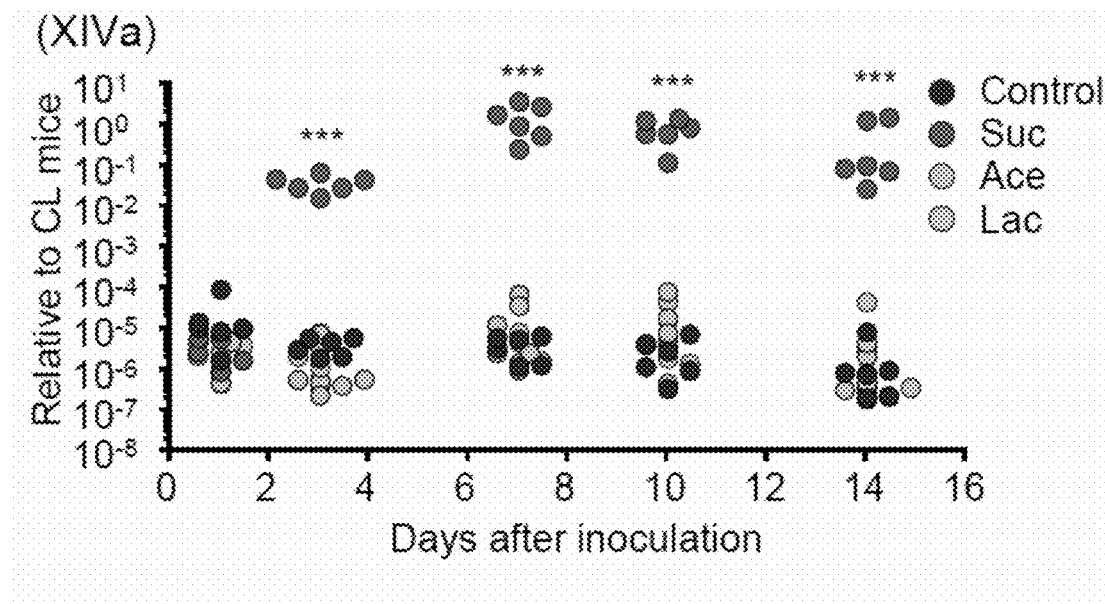
Figure 4E:
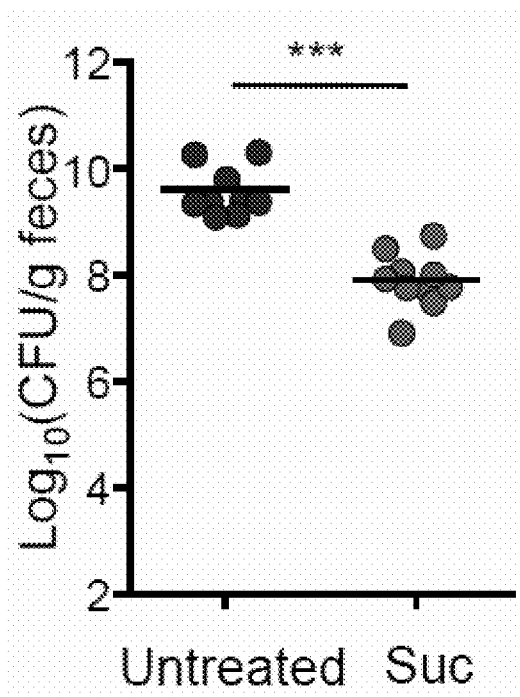
Figure 4F:
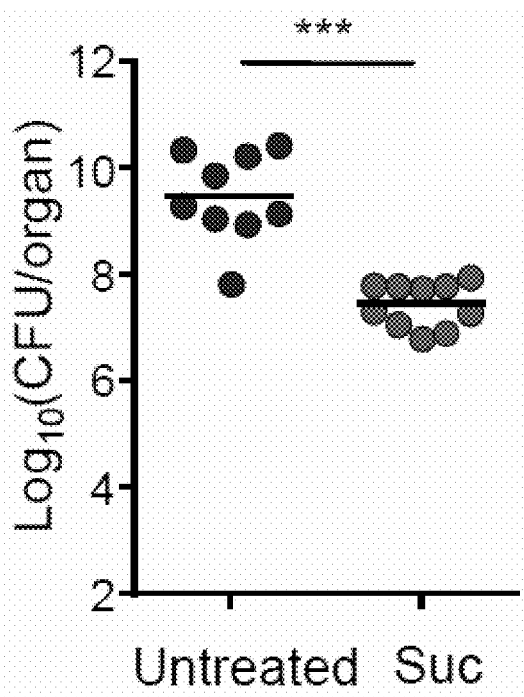
Figure 9A:
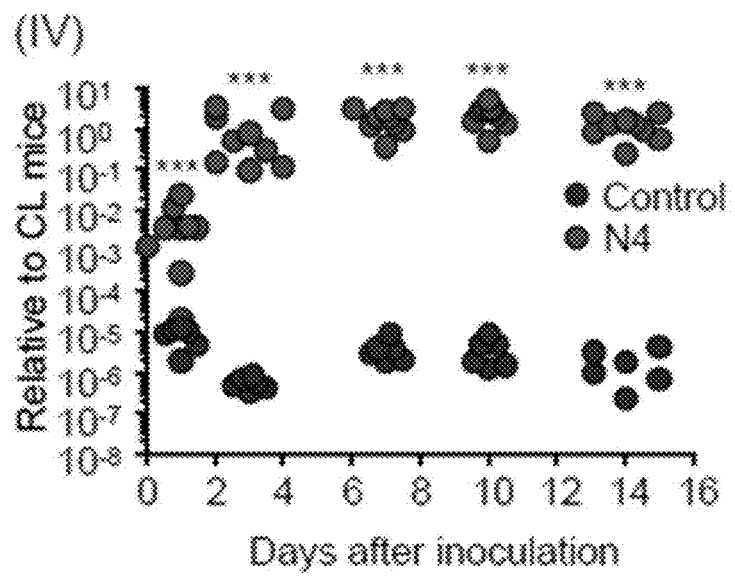
FIGS. 9A-C. Early intestinal colonizers and succinate contribute to the acquisition of protective Clostridia in the gut.
Figure 9B:
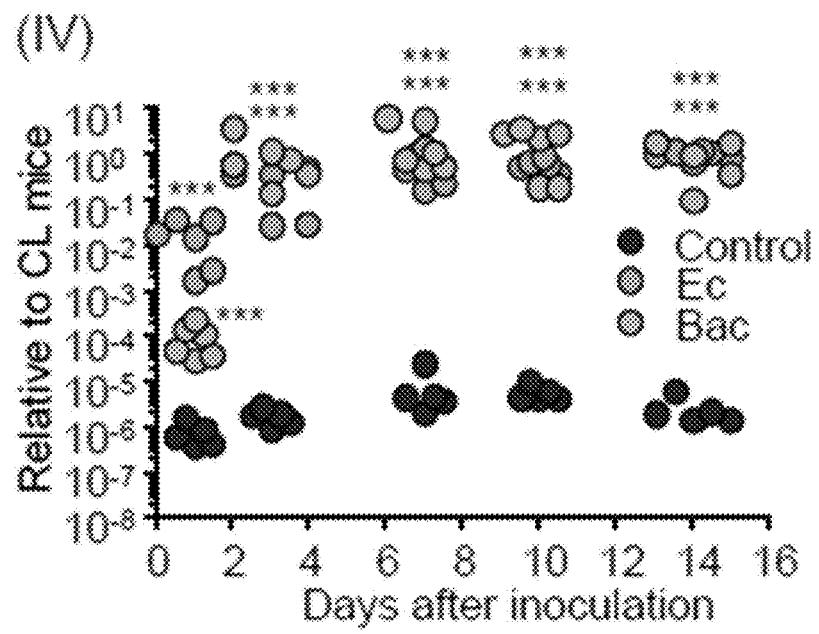
Figure 9C:
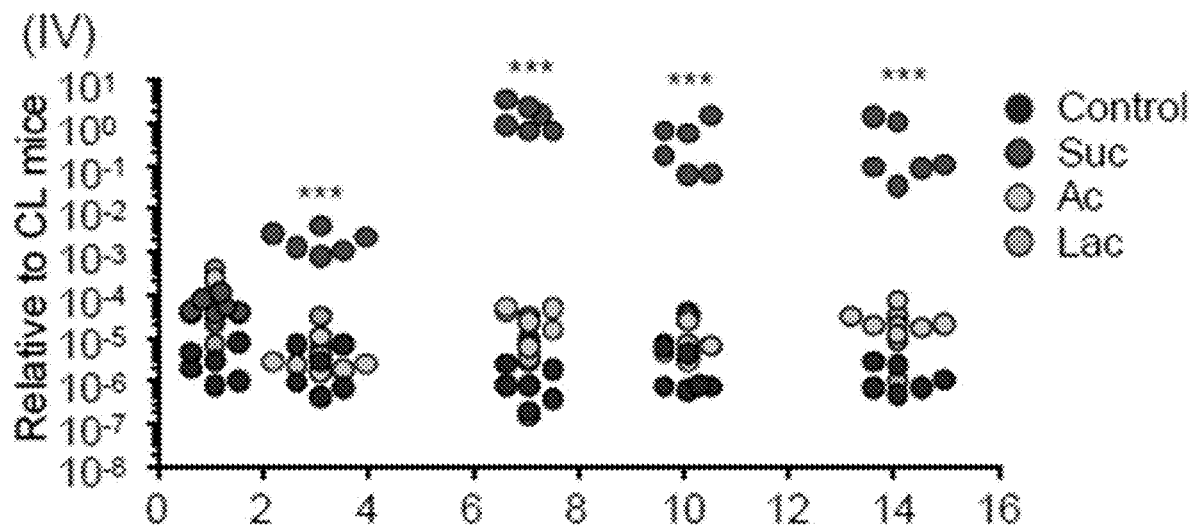
Figure 10:
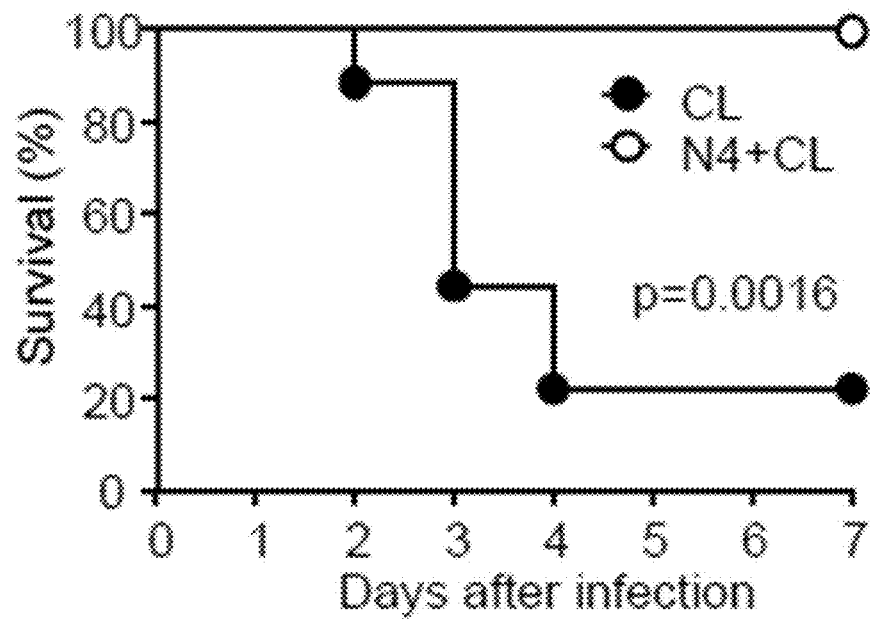

With the exception of a few Lachnospiraceae OTUs, which are present in the microbiota of 12-day old mice, taxa in the order of Clostridiales are absent from the microbiota of 4-day old and 12-day old mice but robustly colonize the intestine between day 12 and 16 of neonatal life, the timeframe associated with the acquisition of colonization resistance against pathogens. To assess whether neonatal bacteria promote the colonization of Clostridia species, GF mice were first colonized with the microbiota from 4-day old mice and seven days later they were gavaged with the Clostridia consortium. Remarkably, the abundance of *Clostridium* IV and XIVa clusters which constitute the predominant Clostridia in the consortium assessed by qPCR was low after intragastric gavage to GF mice (FIG. 4A and FIG. 9A). In the presence of the 4-day neonatal microbiota, the intestinal colonization of Clostridia increased by approximately 6 logs (FIG. 4A and FIG. 9A). Consistent with reduced colonization of Clostridia in the absence of neonatal bacteria, intragastric administration of Clostridia to GF mice reconstituted with the microbiota of 4-day old mice induced robust colonization resistance against *S. Typhimurium* whereas the microbiota of 4-day old mice did not (FIG. 10). Likewise, pre-inoculation of GF mice with *E. coli*, a species which is present in the 4-day and 12-day old neonatal microbiota or a mixture of *Bacteroides* species whose colonization coincides with robust acquisition of Clostridiales in the microbiota of 16-day old mice, enhanced the colonization of Clostridia by 5 to 6 logs (FIG. 4B and FIG. 9B). To assess whether bacteria-derived metabolites regulate intestinal colonization by Clostridia, unbiased capillary electrophoresis-time-of-flight mass spectrometry (CE-TOFMS)-based metabolome analysis was performed of the cecal contents of GF mice and GF mice colonized with dominant bacterial species present in the ceca of neonatal and adult mice. The metabolome analysis revealed that the amounts of succinate were very low in the cecal contents of GF mice. Succinate levels were also low in GF mice reconstituted with Clostridia, slightly increased in GF mice colonized with *E. coli* and robustly increased in GF colonized with *Bacteroides* when compared to GF mice (FIG. 4C). Administration of succinate, but not acetate or lactate, in the drinking water enhanced colonization of Clostridia belonging to the dominant IV and XIVa clusters by 4 to 5-logs (FIG. 4D and FIG. 9C). Consistent with these results, administration of succinate in the drinking water reduced the intestinal loads of the *S. Typhimurium* ΔspiA by ~100-fold in GF mice treated with succinate and given the Clostridia consortium by gavage (FIG. 4E, F). These results indicate that the neonatal microbiota contribute to the acquisition of protective Clostridia prior to weaning and that succinate is sufficient to enhance Clostridia colonization. Collectively, these results demonstrates that acquisition of Clostridia species is a critical event to inhibit the growth of enteric pathogens in the gut. The results indicate that strategies to increase the number of protective Clostridia species are beneficial for the prevention or treatment of enteric infections.

REFERENCES

The following references are herein incorporated by reference in their entireties.

1. C. F. Lanata et al., Global causes of diarrheal disease mortality in children <5 years of age: a systematic review. PLoS One 8, e72788 (2013).
2. M. PrabhuDas et al., Challenges in infant immunity: implications for responses to infection and vaccines. Nat Immunol 12, 189-194 (2011).
3. T. R. Kollmann, O. Levy, R. R. Montgomery, S. Goriely, Innate immune function by Toll-like receptors: distinct responses in newborns and the elderly. Immunity 37, 771-783 (2012).
4. N. Kamada, S. U. Seo, G. Y. Chen, G. Nunez, Role of the gut microbiota in immunity and inflammatory disease. Nat Rev Immunol 13, 321-335 (2013).
5. T. Tanoue, K. Atarashi, K. Honda, Development and maintenance of intestinal regulatory T cells. Nat Rev Immunol 16, 295-309 (2016).
6. P. T. McKenney, E. G. Pamer, From Hype to Hope: The Gut Microbiota in Enteric Infectious Disease. Cell 163, 1326-1332 (2015).
7. M. Hasegawa et al., Transitions in oral and intestinal microbiota composition and innate immune receptor-dependent stimulation during mouse development. Infect Immun 78, 639-650 (2010).
8. C. Palmer, E. M. Bik, D. B. DiGiulio, D. A. Relman, P. O. Brown, Development of the human infant intestinal microbiota. PLoS Biol 5, e177 (2007).
9. R. Figueira, D. W. Holden, Functions of the *Salmonella* pathogenicity island 2 (SPI-2) type III secretion system effectors. Microbiology 158, 1147-1161 (2012).
10. H. Ochman, F. C. Soncini, F. Solomon, E. A. Groisman, Identification of a pathogenicity island required for *Salmonella* survival in host cells. Proc Natl Acad Sci USA 93, 7800-7804 (1996).
11. D. Borenshtein, M. E. McBee, D. B. Schauer, Utility of the *Citrobacter rodentium* infection model in laboratory mice. Curr Opin Gastroenterol 24, 32-37 (2008).

12. A. T. Stefka et al., Commensal bacteria protect against food allergen sensitization. Proc Natl Acad Sci USA 111, 13145-13150 (2014).
13. L. A. Dieleman et al., Chronic experimental colitis induced by dextran sulphate sodium (DSS) is characterized by Th1 and Th2 cytokines. Clin Exp Immunol 114, 385-391 (1998).
14. J. J. Kozich, S. L. Westcott, N. T. Baxter, S. K. Highlander, P. D. Schloss, Development of a dual-index sequencing strategy and curation pipeline for analyzing amplicon sequence data on the MiSeq Illumina sequencing platform. Appl Environ Microbiol 79, 5112-5120 (2013).
15. P. D. Schloss et al., Introducing mothur: open-source, platform-independent, community-supported software for describing and comparing microbial communities. Appl Environ Microbiol 75, 7537-7541 (2009).
16. Q. Wang, G. M. Garrity, J. M. Tiedje, J. R. Cole, Naive Bayesian classifier for rapid assignment of rRNA sequences into the new bacterial taxonomy. Appl Environ Microbiol 73, 5261-5267 (2007).
17. K. Matsuda et al., Establishment of an analytical system for the human fecal microbiota, based on reverse transcription-quantitative PCR targeting of multicopy rRNA molecules. Appl Environ Microbiol 75, 1961-1969 (2009).
18. A. Hirayama et al., Metabolic profiling reveals new serum biomarkers for differentiating diabetic nephropathy. Anal Bioanal Chem 404, 3101-3109 (2012).
19. M. Sugimoto, D. T. Wong, A. Hirayama, T. Soga, M. Tomita, Capillary electrophoresis mass spectrometry-based saliva metabolomics identified oral, breast and pancreatic cancer-specific profiles. Metabolomics 6, 78-95 (2010).

The invention claimed is:

1. A pharmaceutical composition comprising therapeutically effective amounts of non-pathogenic bacteria of 25 or more different species from the class Clostridia and a pharmaceutically acceptable carrier.

2. The pharmaceutical composition of claim 1, comprising an effective amount of the non-pathogenic bacteria for treating or decreasing susceptibility to enteric infection in a subject.

3. The pharmaceutical composition of claim 1, further comprising a probiotic or a prebiotic.

4. The pharmaceutical composition of claim 1, formulated for administration to a human newborn, neonate, or infant.

5. The pharmaceutical composition of claim 1, formulated for administration to a livestock animal.

6. The pharmaceutical composition of claim 1, formulated for administration to a chicken.

7. The pharmaceutical composition of claim 1, formulated for administration to a cow, goat, pig, or sheep.

8. The pharmaceutical composition of claim 1, wherein the non-pathogenic bacteria are alive.

9. The pharmaceutical composition of claim 1, formulated for oral administration.

10. The pharmaceutical composition of claim 1, formulated for rectal administration.

11. The pharmaceutical composition of claim 1, wherein the pharmaceutical composition is a nutraceutical or a food.

12. A kit comprising a pharmaceutical composition according to claim 1.

13. A kit for treating enteric infection in a subject, the kit comprising:
   a) a pharmaceutical composition of claim 1; and
   b) a reagent for testing the membership or relative abundance of one or more members of the gut microbiota of the subject.

14. The kit of claim 13, wherein the reagent comprises a labeled oligonucleotide probe.

15. The kit of claim 13, wherein the reagent comprises an amplification oligonucleotide.

16. The kit of claim 13, wherein the reagent is a test reagent for the presence, absence, or level of Clostridia in the gut microbiota of the subject.

17. The kit of claim 13, wherein the reagent is a test reagent for the membership or relative abundance of Clostridia in the gut microbiota of the subject.

18. The kit of claim 13, wherein the reagent is a test reagent for the presence, absence, or level of a pathogen causative of enteric disease.

* * * * *

SEQUENCE LISTING

```
Sequence total quantity: 4
SEQ ID NO: 1            moltype = DNA  length = 16
FEATURE                 Location/Qualifiers
source                  1..16
                        mol_type = other DNA
                        organism = synthetic construct
SEQUENCE: 1
gcacaagcag tggagt                                                         16

SEQ ID NO: 2            moltype = DNA  length = 18
FEATURE                 Location/Qualifiers
source                  1..18
                        mol_type = other DNA
                        organism = synthetic construct
SEQUENCE: 2
cttcctccgt tttgtcaa                                                       18

SEQ ID NO: 3            moltype = DNA  length = 20
FEATURE                 Location/Qualifiers
source                  1..20
                        mol_type = other DNA
                        organism = synthetic construct
SEQUENCE: 3
aaatgacggt acctgactaa                                                     20

SEQ ID NO: 4            moltype = DNA  length = 22
FEATURE                 Location/Qualifiers
source                  1..22
                        mol_type = other DNA
                        organism = synthetic construct
SEQUENCE: 4
ctttgagttt cattcttgcg aa                                                  22
```